(12) United States Patent
Bao et al.

(10) Patent No.: US 7,081,336 B2
(45) Date of Patent: Jul. 25, 2006

(54) DUAL RESONANCE ENERGY TRANSFER NUCLEIC ACID PROBES

(75) Inventors: Gang Bao, Mableton, GA (US); Andrew Tsourkas, Atlanta, GA (US); Yangqing Xu, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 590 days.

(21) Appl. No.: 10/179,730

(22) Filed: Jun. 25, 2002

(65) Prior Publication Data

US 2003/0129611 A1 Jul. 10, 2003

Related U.S. Application Data

(60) Provisional application No. 60/303,258, filed on Jul. 3, 2001, provisional application No. 60/300,672, filed on Jun. 25, 2001.

(51) Int. Cl.
*C12Q 1/68* (2006.01)

(52) U.S. Cl. .................. 435/6; 536/24.3; 536/24.32; 536/25.32

(58) Field of Classification Search ............ 435/6; 536/24.32, 25.32
See application file for complete search history.

(56) References Cited

U.S. PATENT DOCUMENTS

| | | | |
|---|---|---|---|
| 4,996,143 A | 2/1991 | Heller et al. ............. | 435/6 |
| 5,459,243 A | 10/1995 | Acevedo et al. .......... | 534/565 |
| 5,538,848 A | 7/1996 | Livak et al. .............. | 435/6 |
| 5,866,336 A | 2/1999 | Nazarenko et al. ........ | 435/6 |
| 5,876,930 A | 3/1999 | Livak et al. .............. | 435/6 |
| 5,891,016 A | 4/1999 | Utsui et al. .............. | 600/181 |
| 5,925,517 A | 7/1999 | Tyagi et al. .............. | 435/6 |
| 6,037,130 A | 3/2000 | Tyagi et al. .............. | 435/6 |
| 6,103,476 A | 8/2000 | Tyagi et al. .............. | 435/6 |
| 6,117,635 A | 9/2000 | Nazarenko et al. ........ | 435/6 |
| 6,150,097 A | 11/2000 | Tyagi et al. .............. | 435/6 |
| 6,177,555 B1 | 1/2001 | Jayasena et al. .......... | 536/23.1 |
| 6,228,592 B1 | 5/2001 | Tsuji et al. .............. | 435/6 |
| 6,248,518 B1 | 6/2001 | Parkhurst et al. ......... | 435/6 |

FOREIGN PATENT DOCUMENTS

| | | |
|---|---|---|
| EP | 0070685 A2 | 1/1983 |
| EP | 0 971 038 A1 | 1/2000 |
| WO | WO 99/49293 | 9/1999 |

OTHER PUBLICATIONS

Matthews, et al; "Analytical Strategies for the Use of DNA Probes", Analytical Biochemistry vol. 169, pp. 1-25, 1988.
Tyagi, et al. "Molecular Beacons: Probes that Fluoresce upon Hybridization", Nature Biotechnology, vol. 14, pp. 303-308, Mar. 1996.
Tsourkas, et al., "Detecting mRNA Transcripts using Fret-Enhanced Molecular Beacons", BED-vol. 50, 2001, Bioengineering Conference, 2001.
Cardullo, et al., "Detection of Nucleic Acid Hybridization by Nonradiative Fluorescence Resonance Energy Transfer", Proc. Natl. Acad. Sci. USA, vol. 85, pp. 8790-8794, Dec. 1988.
Sokol et al., "Real time detection of DNA-RNA hybridization in living cells", *Proc. Natl. Acad. Sci.*, 95:11538-11543 (1998).
Mergny, et al., Fluorescence energy transfer as a probe for nucleic acid structures and sequences, *Nucleic Acids Research*, 22(6):920-928 (1994).
Sixou, et al., "Intracellular oligonucleotide hybridization detected by fluorescence resonance energy transfer (FRET)", *Nucleic Acids Research*, 22(4):662-668 (1994).
Tsuji et al., 2000, "Direct Observation of Specific Messenger RNA in a Single Living Cell under a Fluorescene Microscope," *Biophysical Journal*, 78:3260-3274.
Wittwer et al., 1997, "Continuous Fluorecence Monitoring of Rapid Cycle DNA Amplification," *BioTechniques*, 22(1):130-138.

*Primary Examiner*—James Martinell
(74) *Attorney, Agent, or Firm*—Sutherland Asbill & Brennan LLP

(57) ABSTRACT

Dual nucleic acid probes with resonance energy transfer moieties are provided. In particular, fluorescent or luminescent resonance energy transfer moieties are provided on hairpin stem-loop molecular beacon probes that hybridize sufficiently near each other on a subject nucleic acid, e.g. mRNA, to generate an observable interaction. The invention also provides lanthanide chelate luminescent resonance energy transfer moieties on linear and stem-loop probes that hybridize sufficiently near each other on a subject nucleic acid to generate an observable interaction. The invention thereby provides detectable signals for rapid, specific and sensitive hybridization determination in vivo. The probes are used in methods of detection of nucleic acid target hybridization for the identification and quantification of tissue and cell-specific gene expression levels, including response to external stimuli, such as drug candidates, and genetic variations associated with disease, such as cancer.

50 Claims, 9 Drawing Sheets

(a)

SEQ ID NO:24
(Stem-loop)

3'-AGTA CTCAGGAAGGTGCTATGG TTCA-5'

SEQ ID NO:25 (Target)

(b)

SEQ ID NO:26
(Stem-loop)

3'-AGTA CTCAGGAAGGTGCTATGG TTCA-5'

SEQ ID NO:25 (Target)

SEQUENCE LISTING

```
<160> NUMBER OF SEQ ID NOS: 37

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Probe

<400> SEQUENCE: 1
ccacatgatg gcatggactg tgg                                             23

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Probe

<400> SEQUENCE: 2
tgatggcatg gactgtgg                                                   18

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Probe

<400> SEQUENCE: 3
gagtccttcc acgataccga ctc                                             23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Probe

<400> SEQUENCE: 4
gagtccttcc acgataccga ctc                                             23

<210> SEQ ID NO 5
<211> LENGTH: 23
<212> TYPE: DNA
<213> ORGANISM: Artificial Sequence
```

```
<220> FEATURE:
<223> OTHER INFORMATION: Description of Artificial Sequence: Probe

<400> SEQUENCE: 5
gagtccttcc acgataccga ctc                                              23

<210> SEQ ID NO 6
<211> LENGTH: 49
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 6
actttggtat cgtggaagga ctcataccac agtccatgcc atcactgcc                  49

<210> SEQ ID NO 7
<211> LENGTH: 50
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 7
actttggtat cgtggaagga ctcatgacca cagtccatgc catcactgcc                 50

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 8
actttggtat cgtggaagga ctcattgacc acagtccatg ccatcactgc c               51

<210> SEQ ID NO 9
<211> LENGTH: 52
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 9
actttggtat cgtggaagga ctcatttgac cacagtccat gccatcactg cc              52

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 10
tgacaacttt ggtatcgtgg aaggactcat gaccacagtc catgccatca ctgccaccca      60

<210> SEQ ID NO 11
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 11
gagtccttcc acgataccag actc                                               24

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ccacatgatg gcatggactg tgg                                                23

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Probe

<400> SEQUENCE: 13
gagtccttcc acgataccac tc                                                 22

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Probe

<400> SEQUENCE: 14
gagtccttcc acgataccag actc                                               24

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Probe

<400> SEQUENCE: 15
gagtccttcc acgataccag gactc                                              25

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Probe

<400> SEQUENCE: 16
cctcgagtcc ttccacgata ccagagg                                            27

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Probe
```

```
<400> SEQUENCE: 17
ctgacgagtc cttccacgat accagtcag                                    29

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 18
ctgagcgagt ccttccacga taccagctca                                   30

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 19
actttggtat cgtggaagga ctcatga                                      27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 20
actttggtat cgtggaagga atcatga                                      27

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 21
actttggtat cgtagaagga ctcatga                                      27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 22
actttggtat cgtagaagga atcatga                                      27

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      target oligonucleotide
```

```
<400> SEQUENCE: 23
actttggtat cgtaaaagga ctcatga                                              27

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gagtccttcc acgtaaccag gactc                                                25

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 25
actttggtat cgtggaagga ctcatga                                              27

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gagtccttcc acgataccac tc                                                   22

<210> SEQ ID NO 27
<211> LENGTH: 78
<212> TYPE: DNA
<213> ORGANISM: Homo sapiens

<400> SEQUENCE: 27
atgactgaat ataaacttgt ggtagttgga gctggtggcg taggcaagag tgccttgacg          60
atacagctaa ttcagaat                                                        78

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
agtgcgctgt atcgtcaagg cact                                                 24

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 29
cctacgccat cagctccgta gg                                            22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cctacgccaa cagctccgta gg                                            22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cctacgccac gagctccgta gg                                            22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cctacgccac aagctccgta gg                                            22

<210> SEQ ID NO 33
<211> LENGTH: 121
<212> TYPE: DNA
<213> ORGANISM: Homo sapiens

<400> SEQUENCE: 33
atgggtgccc cgacgttgcc ccctgcctgg cagcccttc tcaaggacca ccgcatctct    60
acattcaaga actggccctt cttggagggc tgcgcctgca ccccggagcg gatggccgag   120
g                                                                   121

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ccttgagaaa gggctgccca agg                                           23

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 35
ccgcattgaa tgtagagatg cgg                                              23

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Probe

<400> SEQUENCE: 36
acctggatgt tgtcctcgtc aggt                                             24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Probe

<400> SEQUENCE: 37
aagattgaag accttggcga tctt                                             24
```

DUAL RESONANCE ENERGY TRANSFER NUCLEIC ACID PROBES

CROSS REFERENCE TO RELATED APPLICATIONS

The present invention claims the priority benefit of U.S. Provisional Patent Application Ser. No. 60/300,672 filed Jun. 25, 2001 and U.S. Provisional Patent Application Ser. No. 60/303,258 filed Jul. 3, 2001, the entire contents of which are hereby incorporated by reference.

FIELD OF THE INVENTION

This invention relates generally to the detection of target nucleic acids, such as mRNA. More specifically, the present invention relates to a dual molecular beacons approach that uses resonance energy transfer to significantly reduce false-positive signal in detection of target nucleic acids associated with disease.

BACKGROUND OF THE INVENTION

The ability to monitor and quantify the level of gene expression in living cells in real time can provide important information concerning the production, temporal and spatial processing, localization, and transport of specific mRNA in different conditions. This new type of information could potentially revolutionize biological studies and may also have applications in medical diagnostics and therapeutics. Technologies currently available for analysis and quantification of gene expression such as real-time RT-PCR, Northern blotting, expressed sequence tag (EST), serial analysis of gene expression (SAGE) and DNA microarrays are powerful tools for in vitro studies; however, they are not capable of quantifying gene expression in living cells. There is a clear need to develop molecular probes that can recognize target mRNA in living cells with high specificity and instantaneously convert such recognition into a measurable signal with a high signal-to-background ratio.

Molecular beacons are a class of fluorescence-quenched nucleic acid probes that can be used in a quantitative fashion; these probes fluoresce upon target recognition (i.e., hybridization) with potential signal enhancement of >200 under ideal conditions. Structurally, they are dual-labeled oligonucleotides with a reporter fluorophore at one end and a dark quencher at the opposite end (Tyagi and Kramer; 1996). They are designed to have a target-specific probe sequence positioned centrally between two short self-complementary segments which, in the absence of target, anneal to form a stem-loop hairpin structure that brings the fluorophore in close proximity with the quencher. In this configuration the molecular beacon is in the "dark" state (Bemacchi and Mely, 2001). The hairpin opens upon hybridization with a complementary target, physically separating the fluorophore and quencher. In this configuration the molecular beacon is in the "bright" state. Transition between dark and bright states allows for differentiation between bound and unbound probes and transduces target recognition into a fluorescence signal (Matsuo, 1998; Liu et al., 2002).

Linear fluorescent probes, as are used in fluorescence in-situ hybridization (FISH) (Femino et al., 1998), are "bright" in both the bound and unbound state. To detect positive signal after hybridization, unbound probe must be removed by washing, which prevents the application of this method to gene detection in living cells. In theory, molecular beacons do not require a washing step and so should be directly usable in living cells (Matsuo, 1998; Sokol et al., 1998). However, interaction between molecular beacons and certain intracellular factors can cause fluorescence in the absence of target hybridization and lead to false-positive signals (Mitchell, 2001). Using conventional molecular-beacon-based methods, the fluorescent signal that results from target hybridization cannot be distinguished from any other event that spatially separates reporter from quencher, such as probe degradation by intracellular nucleases or interaction with DNA binding proteins that unwind the hairpin stem structure (Li et al., 2000; Dirks et al., 2001; Molenaar, et al., 2001; Fang et al., 2000).

Two linear oligonucleotide probes labeled respectively with donor and acceptor fluorophores have been used in FRET-based studies of DNA hybridization, DNA secondary structure and RNA synthesis (Cardullo et al., 1988; Morrison and Stols, 1993; Sixou et al., 1994; Sei-Iida et al., 2000; Tsuji et al. 2000; Tsuji et al. 2001), however, the sensitivity of intracellular gene detection using such probes suffers from strong background signal due to unbound probes and cell autofluorescence.

The unique target recognition and signal transduction capabilities of molecular beacons have led to their application in many biochemical and biological assays including quantitative PCR (Vogelstein and Kinzler, 1999; Chen and Mulchandani, 2000), protein-DNA interactions (Fang et al., 2000; Li et al., 2000), multiplex genetic analysis (Marras et al., 1999; de Baar et al., 2001), and the detection of mRNA in living cells (Matsuo 1988; Sokol et al., 1998; Molenaar 2001). However, false-positive signals due to protein-beacon interaction and nuclease-induced beacon degradation significantly limit the sensitivity of the in vivo applications (Mitchell, 2001). The thermodynamic and kinetic properties of molecular beacons are dependent on its structure and sequence in complex ways (Bonnet et al. 1999; Kuhn et al., 2002). Moreover, the signal-to-background ratio in target detection is dependent not only on design (length and sequence of the stem and probe) but also on the quality of oligonucleotide synthesis and purification (Goddard et al., 2000; Bonnet et al., 1998) and the assay conditions employed.

Therefore, there is a strong need in the art to provide improved compositions and methods for improved detection of nucleic acids that exhibit high specificity and sensitivity. Furthermore, there is a need for such compositions and methods that can be used for detection of genetic transcription in vivo. There is a need for such improved compositions and methods for observing changes in genetic expression levels in response to external stimuli, or for the detection of genetic abnormalities indicating a potential or actual disease state.

SUMMARY OF THE INVENTION

The present invention provides compositions for the detection of a subject nucleic acid comprising a first nucleic acid probe that hybridizes to a first nucleic acid target sequence on the subject nucleic acid, forms a stem-loop structure when not bound to the first nucleic acid target sequence, and incorporates a resonance energy transfer donor moiety. This embodiment of the invention further provides a second nucleic acid probe that hybridizes to a second nucleic acid target sequence on the subject nucleic acid, forms a stem-loop structure when not bound to the second nucleic acid target sequence, and incorporates a resonance energy transfer acceptor moiety. The invention provides that the first nucleic acid target sequence and the second nucleic acid target sequence are separated by a number of nucleotides on the subject nucleic acid such that a resonance energy transfer signal from interaction between the donor moiety of the first nucleic acid probe and the acceptor moiety of the second nucleic acid probe can be detected to determine hybridization of both the first nucleic acid probe and the second nucleic acid probe to the subject nucleic acid.

Therefore, according to the present invention, alternative compositions and methods are provided for the detection of subject nucleic acid sequences of interest in a sample. In particularly preferred embodiments, fluorescent or luminescent resonance energy transfer moieties are provided on hairpin stem-loop molecular beacon probes that hybridize sufficiently near each other on a subject nucleic acid, e.g. mRNA, to generate an observable interaction. The invention thereby provides signal of energy transfer for rapid, specific and sensitive hybridization detection that can be advantageously used in vivo. The probes are useful in methods of detection of target nucleic acid hybridization and the identification of genetic expression and the presence of genetic variations associated with disease, such as cancer.

Accordingly, it is an object of the present invention to provide improved compositions and methods of use for more sensitive, specific or rapid nucleic acid detection.

It is a further object of the present invention to provide improved methods for the detection of gene expression associated with a response to external stimuli, e.g. a therapeutic drug candidate.

It is a further object of the present invention to provide improved methods for the detection of gene expression, including genetic expression associated with a disease state.

It is another object of the present invention to provide for the use of such compositions and method in vivo.

These and other objects, features and advantages of the present invention will become apparent after a review of the following detailed description of the disclosed embodiments and the appended claims.

BRIEF DESCRIPTION OF THE FIGURES

FIG. 11a shows Conventional molecular beacons have stem sequences that are independent of the target sequence. FIG. 11b shows shared-stem molecular beacons are designed such that one arm of the stem participates in both hairpin formation and target hybridization.

FIG. 12a shows the design of a molecular beacon with a probe length of 19 bases and a stem length of 6 bases inadvertently resulted in additional bases participating in stem formation (circles). FIG. 12a shows the design of a molecular beacon with a probe length of 18 bases and a stem length of 4 bases inadvertently resulted in an additional base participating in target hybridization (circle).

FIG. 17a shows melting curves for conventional and shared-stem molecular beacons in the presence of wild-type (solid line) and mutant (dashed line) target. FIG. 17b shows the difference in the fraction of conventional or shared-stem molecular beacons bound to wild-type and mutant targets.

DETAILED DESCRIPTION OF THE INVENTION

Figure 1:
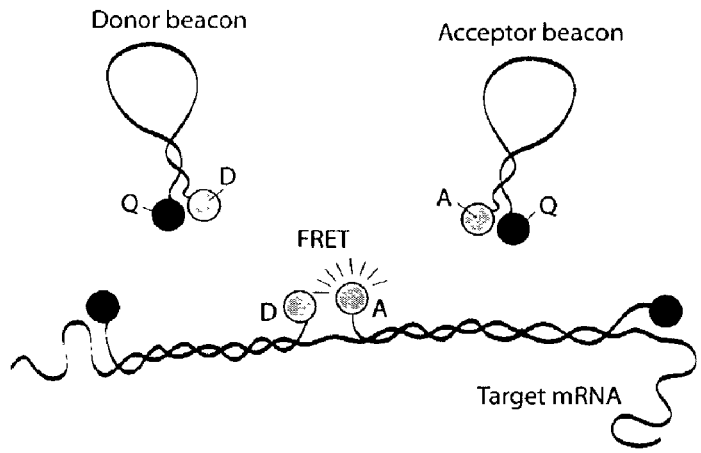
FIG. 1 shows hybridization of the donor and acceptor molecular beacons to adjacent regions on the same mRNA target results in FRET. By detecting FRET, fluorescence signals due to probe/target binding can be distinguished from that due to beacon degradation and non-specific interactions. In the figure, letters Q, D and A represent respectively quencher, donor dye and acceptor dye molecules.

The present invention may be understood more readily by reference to the following detailed description of the preferred embodiments of the invention and the Examples included therein. Before the present compounds, compositions, and methods are disclosed and described, it is to be understood that this invention is not limited to any specific nucleic acid probes, specific nucleic acid targets, specific cell types, specific conditions, or specific methods, etc., as such may, of course, vary, and the numerous modifications and variations therein will be apparent to those skilled in the art. It is also to be understood that the terminology used herein is for the purpose of describing particular embodiments only and is not intended to be limiting. As used in the specification and in the claims, "a" or "an" can mean one or more, depending upon the context in which it is used. Thus, for example, reference to "a nucleic acid probe" can mean that one or more than one nucleic acid probe can be utilized.

In accordance with the purpose(s) of this invention, as embodied and broadly described herein, this invention, in one aspect, provides a composition for the detection of a subject nucleic acid comprising, a first nucleic acid probe that hybridizes to a first nucleic acid target sequence on the subject nucleic acid, forms a stem-loop structure when not bound to the first nucleic acid target sequence, and incorporates a resonance energy transfer donor moiety. This embodiment of the invention further provides a second nucleic acid probe that hybridizes to a second nucleic acid target sequence on the subject nucleic acid, forms a stem-loop structure when not bound to the second nucleic acid target sequence, and incorporates a resonance energy transfer acceptor moiety. The invention provides that the first nucleic acid target sequence and the second nucleic acid target sequence are separated by a number of nucleotides on the subject nucleic acid such that a resonance energy transfer signal from interaction between the donor moiety of the first nucleic acid probe and the acceptor moiety of the second nucleic acid probe can be detected to determine hybridization of both the first nucleic acid probe and the second nucleic acid probe to the subject nucleic acid. Preferably, the resonance energy transfer signal is a florescent or luminescent signal.

In an alternative embodiment, the invention provides a first nucleic acid probe that hybridizes to a first nucleic acid target sequence on the subject nucleic acid, and incorporates a luminescence resonance energy transfer lanthanide chelate donor moiety; and second nucleic acid probe that hybridizes to a second nucleic acid target sequence on the subject nucleic acid, and incorporates an organic resonance energy transfer acceptor moiety, wherein the first nucleic acid target sequence and the second nucleic acid target sequence are separated by a number of nucleotides on the subject nucleic acid such that a luminescence resonance energy transfer signal from interaction between the lanthanide chelate donor moiety of the first nucleic acid probe and the acceptor moiety of the second nucleic acid probe can be detected to determine hybridization of both the first nucleic acid probe and the second nucleic acid probe to the subject nucleic acid. In certain embodiments of this invention, the first nucleic acid probe or second nucleic acid probe is linear or randomly coiled when not hybridized to the first or second nucleic acid target sequences, respectively. In other embodiments of this invention, the first nucleic acid probe or second nucleic acid probe forms a stem-loop structure when not hybridized to the first or second nucleic acid target sequences, respectively.

In certain preferred embodiments of the invention, the first nucleic acid probe further incorporates a quencher moiety, such that an interaction between the donor moiety of the first nucleic acid probe and the quencher moiety can be detected to differentiate between the first nucleic acid probe in the stem-loop structure and non-stem-loop structure. Similarly, in other embodiments, the second nucleic acid probe further incorporates a quencher moiety, such that an interaction between the acceptor moiety of the second nucleic acid probe and the quencher moiety can be detected to differentiate between the second nucleic acid probe in the stem-loop structure and non-stem-loop structure. In embodiments utilizing a quencher moiety on a nucleic acid probe, the invention provides that the quencher moiety can be selected from, for example, dabcyl quencher, black hole quencher or Iowa Black quencher or other moieties well-known in the art to change the resonance energy transfer wavelength emission of an unquenched donor or acceptor moiety.

In certain other embodiments, the first nucleic acid probe further incorporates a resonance energy transfer moiety pair, such that a resonance energy transfer signal from interaction between the donor moiety and the acceptor moiety on the first nucleic acid probe can be detected to differentiate between the first nucleic acid probe in the stem-loop structure and non-stem-loop structure. Similarly, other embodiments provide that the second nucleic acid probe further incorporates a resonance energy transfer moiety pair, such that a resonance energy transfer signal from interaction between the donor moiety and the acceptor moiety on the second nucleic acid probe can be detected to differentiate between the second nucleic acid probe in the stem-loop structure and non-stem-loop structure.

In various embodiments, the first nucleic acid target and the second nucleic acid target are separated by 1 to 20 nucleotides, or separated by 2, 3, 4, 5, 6, 7, 8, 9, 10, 11, 12, 13, 14, or 15 nucleotides. As discussed below, the preferred number of separating nucleotides will vary depending upon the resonance energy transfer source used, and can be routinely determined by one of skill in the art in view of the present disclosure.

In preferred embodiments, the resonance energy signals are due to fluorescence resonance energy transfer (FRET) or luminescence resonance energy transfer (LRET). In embodiments wherein the resonance energy transfer signal is due to fluorescence resonance energy transfer, the donor moiety can be for example a 6-Fam fluorophore. In embodiments wherein the resonance energy transfer signal is due to fluorescence resonance energy transfer, the acceptor moieties can be Cy-3, ROX or Texas Red. Additional examples of FRET donor and acceptor moieties useful in the present invention are provided below.

In other embodiments, the resonance energy transfer signal is due to luminescence resonance energy transfer (LRET) and the donor moiety is a lanthanide chelate. In some preferred embodiments where the resonance energy signal is due to LRET, the donor moiety can be Europium or Terbium. Furthermore, in some embodiments where the resonance energy signal is due to LRET, the donor moiety can be a lanthanide chelate such as DTPA-cytosine, DTPA-cs124, BCPDA, BHHCT, Isocyanato-EDTA, Quantum Dye, or W1024 and the acceptor moiety can be Cy-3, ROX or Texas Red. In some embodiments, due to the range of effective resonance energy transfer of the lanthanide chelate, multiple acceptor moieties may be employed. The donor moiety can be a lanthanide chelate and the acceptor moiety can be a phycobiliprotein. In certain embodiments, the phycobiliprotein is Red Phycoerythrin (RPE), Blue Phycoerythrin (BPE), or Allophycocyanin (APC). Additional examples of LRET donor and acceptor moieties useful in the present invention are provided below.

In certain embodiments, the invention provides that the first or second nucleic acid probes each comprise from 5 to 50 nucleotides, 10 to 40 nucleotides, or 15, 16, 17, 18, 19, 20, 21, 22, 23, 24, 25, 26, 27, 28, 29 or 30 nucleotides. In other preferred embodiments, the nucleic acid probes comprise a 2'-O-methyl nucleotide backbone, among many alternative or synthetic nucleotides, described below. The invention further provides that one end of the first and/or the second nucleic acid probes participates in both stem-loop formation and hybridization to the target nucleic acid. Such embodiments are referred to herein as a shared-stem molecular beacon, or probe, herein, and are described in more detail below, particularly in Example 2.

In additional embodiments, the invention provides methods for detecting a subject nucleic acid, comprising combining the composition described herein with a sample suspected of containing a subject nucleic acid, and detecting hybridization by differential resonance energy transfer signal to determine the presence or absence, and/or the expression level of the subject nucleic acid in the sample in vitro or in vivo. In some preferred embodiments, the methods can be performed in vivo. Therefore, in a preferred embodiment of this method, the sample contains a living cell. The invention provides that the methods may be performed with samples comprising living tissues and cells that are taken out of the body, or that remain in situ.

The methods of the present invention further include detection of changes in the levels of expression of a nucleic acid target, or in RNA transcript, such that alterations of gene expression can be monitored as a result of the dose-dependent cellular response to external stimuli, such as drug molecules, hormones, growth factors, temperature, shear flow, or microgravity, for example. The invention further provides that the compositions can be used to visualize, i.e., through fluorescence or luminescence, the location and relative amount of gene expression in tissues and cells.

In diagnostic or prognostic detection methods the subject nucleic acid can comprise a genetic point mutation, deletion, or insertion relative to a naturally occurring or control nucleic acid. Such screening methods can permit the detection of the subject nucleic acid indicating the presence of a genetically associated disease, such as certain cancers, in the sample. There are many well-known examples of genetic mutations already in the art that are indicative of a disease state. The methods include the detection of nucleic acids comprising K-ras, survivin, p53, p16, DPC4, or BRCA2. Furthermore, the methods can be used to detect the amount of a subject nucleic acid being produced by an organism for purposes other than diagnosis or prognosis of a disease or condition. Resonance energy transfer detections of the present invention can be performed with the assistance of single- or multiple-photon microscopy, time-resolved fluorescence microscopy or fluorescence endoscopy, as detailed below.

The invention further provides kits for the detection of a subject nucleic acid comprising the nucleic acid probe compositions described herein, necessary reagents and instructions for practicing the methods of detection. Such alternative compositions, methods and kits therefor are described in more detail by way of the examples, and still others will be apparent to one of skill in the art in view of the present disclosure.

Figure 11:
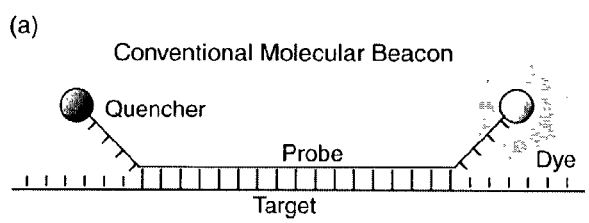
FIGS. 11a and 11b shows alternative molecular beacon designs.
Figure 11:
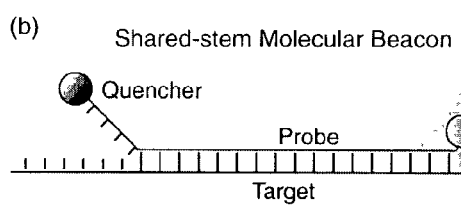

One embodiment of the present invention provides compositions and methods that measure a resonance energy transfer, for example, a fluorescent signal due to FRET or LRET as a result of direct interaction between two molecular beacons when hybridized to the same target nucleic acid of interest. This method can dramatically reduce false-positive signals in gene detection and quantification in living cells. As shown in FIGS. 1 and alternatively in FIG. 11, this approach utilizes a pair of molecular beacons, one with a donor fluorophore and a second with an acceptor fluorophore. Probe sequences are chosen such that the molecular beacons hybridize adjacent to each other on a single nucleic acid target in a way that positions their respective fluorophores in optimal configuration for FRET (Mergny et al., 1994; Sixou et al. 1994). Emission from the acceptor fluorophore serves as a positive signal in the FRET based detection assay.

If acceptor and donor fluorophores are well matched, excitation of the donor can be achieved at a wavelength that has little or no capacity to excite the acceptor; excitation of the acceptor will therefore only occur if both molecular beacons are hybridized to the same target nucleic acid and FRET occurs. Molecular beacons that are degraded or open due to protein interactions will result in the presence of unquenched fluorophore, however, fluorescence emitted from these species is different in character from the signal obtained from donor/acceptor FRET pair, making background and true positive signal more readily differentiated. Thus, by detecting FRET instead of direct single-molecule fluorescence, nucleic acid probe/target binding events can be distinguished from false-positives.

In contrast to prior labeling of two linear oligonucleotide probes with donor and acceptor fluorophores, the stem-loop hairpin structure of molecular beacons offers further reduction in background fluorescence as well as enhanced specificity, which is helpful particularly when detection of allelic variants or point mutations is desired (Bonnet et al., 1999; Tsourkas et al., 2002a).

Further benefit from another embodiment of the dual energy transfer molecular beacons and method of the present invention can be achieved by employing an oligonucleotide probe with a lanthanide chelate as the donor and a molecular beacon with a traditional organic fluorophore as the acceptor (reporter) moiety. In contrast to organic fluorophores that have a fluorescence lifetime of ~10 ns, lanthanide chelates can have emission lifetimes greater than 1 ms (Sueda et al; 2000; Evangelista et al., 1988). The mechanism that is responsible for the long lifetime emission of lanthanide chelates is complex and involves energy transfer from the triplet state of the aromatic ligand. Specifically, upon excitation the ligand is excited to its singlet state and then undergoes an intersystem transition to its triplet state, whereas the energy is either quenched by water molecules or transferred to the lanthanide ion. Fluorescence is then emitted from the lanthanide ion as it returns to the ground state (Lemmetyinen et al., 2000). Since such fluorescence emission does not result from a singlet-to-singlet transition, the use of lanthanide chelates as a donor results in luminescent resonance energy transfer (LRET). Therefore, by using pulse excitation and time-gating techniques, it is possible to selectively record emission after the background fluorescence from organic dyes, scattering, and autofluorescence has decayed (Yuan et al, 1998; Lopez et al, 1993). The only signals remaining in this long-time domain are the emission from the lanthanide chelate and from acceptor fluorophores that have participated in LRET. In this case the narrow emission peaks of a lanthanide chelate render the background fluorescence close to zero at certain wavelengths, leading to extremely large signal-to-background ratio. The donor probe in a LRET pair can be a simple linear probe, i.e., neither quencher nor hairpin structure are necessary.

Furthermore, the invention provides a design variant for molecular beacons where one arm of the stem participates in both hairpin formation and target hybridization, referred to herein as "shared-stem" molecular beacons. In contrast, conventional molecular beacons are designed such that the loop sequence is complementary to the target while the stem sequences are self-complementary but unrelated to the target sequence. This new design offers certain advantages over conventional molecular beacon design, especially in two-probe fluorescence resonance energy transfer (FRET) assays (Cardullo et al., 1998; Sei-Iida et al., 2000; Tsuji et al., 2000; Tsuji et al., 2001; Tsourkas and Bao 2001). The invention provides the thermodynamic and kinetic properties of both shared-stem and conventional molecular beacons and makes a systematic comparison between them. In particular, the present description quantifies the changes in enthalpy and entropy upon the formation of probe/target duplexes as determined by the probe and stem lengths. Further provided herein is a study of the melting behavior, specificity, and hybridization on-rate depend on the stem length of molecular beacons, such that one of skill in the art may make and use a variety of embodiments to suit the specific purposes of each situation.

The nucleic acid probes of the invention utilize the principle of resonance energy transfer between a donor moiety and an acceptor moiety. In a preferred embodiment, the resonance energy transfer is fluorescence resonance energy transfer (FRET), in which the first and second probes are labeled with donor and acceptor moieties, respectively, wherein the donor moiety is a fluorophore and the acceptor moiety may be a fluorophore, such that fluorescent energy emitted by the donor moiety is absorbed by the acceptor moiety when both probes are hybridized to the first and second target sequences respectively on the same nucleic acid subject. In one embodiment of the present invention, the acceptor moiety is a fluorophore that releases the energy absorbed from the donor at a different wavelength; the emissions of the acceptor may then be measured to assess the progress of the hybridization reaction.

In a preferred embodiment, the probe is a hairpin stem-loop structure (often referred to in the art as a molecular beacon) that contains either a donor or acceptor moiety and optionally a quencher moiety, such that the quencher moiety reduces the fluorescence of the donor or acceptor when the probe is in the stem-loop structure (i.e., not hybridized). When the probe is hybridized to the target nucleic acid in this embodiment, its conformation changes, eliminating the quenching effect, and the resulting fluorescence of the donor or acceptor moiety may be detected.

In an alternative embodiment, the present invention provides a nucleic acid probe that forms a hairpin stem-loop structure in which resonance energy transfer will decrease when the probe is hybridized with the target nucleic acid. In such an embodiment, the quencher moiety on the first probe is replaced with a reciprocating moiety to form a resonance energy transfer moiety pair, and the differential in resonance energy transfer is detectable between the hairpin stem-loop structure and a non-stem-loop structure. Alternatively, the quencher moiety on the second probe is replaced with a reciprocating moiety to form a resonance energy transfer moiety pair, and the differential in resonance energy transfer is detectable between the hairpin stem-loop structure and a non-stem-loop structure. In such embodiments of the present invention, a third resonance energy transfer moiety pair forms by the dual probes, a donor moiety on the first probe, and an acceptor moiety on the second probe, such that the resonance energy transfer signal due to the interaction of donor and acceptor may be measured to assess the progress of the hybridization reaction of both probes on the subject nucleic acid.

In another embodiment, the present invention provides that one of the nucleic acid probes is linear (non-stem-loop) and the probes are separately labeled with lanthanide chelator donor and organic acceptor moieties, such that resonance energy transfer will occur when the nucleic acid probes are hybridized. In yet another embodiment, the invention uses a pair of such linear primers, one labeled with a lanthanide donor and another with an organic acceptor moiety, respectively.

One aspect of the invention pertains to nucleic acids sufficient for use as hybridization probes for the identification of a target nucleic acid (e.g., DNA or mRNA). As used herein, the term "nucleic acid" is intended to include DNA molecules (e.g., cDNA or genomic DNA) and RNA molecules (e.g., mRNA) and analogs of the DNA or RNA generated using nucleotide analogs. As referred to herein, nucleic acids that are "complementary" can be perfectly or imperfectly complementary, as long as the desired property resulting from the complementarity is not lost, e.g., ability to hybridize.

The nucleic acids of the present invention may be substantially isolated or alternatively unpurified. An "isolated" or "purified" nucleic acid is one that is substantially separated from other nucleic acid molecules that are present in the natural source of the nucleic acid. Preferably, an "isolated" nucleic acid is substantially free of sequences that naturally flank the nucleic acid (i.e., sequences located at the 5' and 3' ends of the nucleic acid) in the genomic DNA of the organism from which the nucleic acid is derived. Moreover, an "isolated" nucleic acid molecule can be substantially free of other cellular material, or culture medium when produced by recombinant techniques, or chemical precursors or other chemicals when chemically synthesized. (see, Sambrook et al. 1989, *Molecular Cloning: A Laboratory Manual.* 2nd, ed., *Cold Spring Harbor Laboratory*, Cold Spring Harbor Laboratory Press, Cold Spring Harbor, N.Y.).

The probe typically comprises substantially purified nucleic acid. The nucleic acid probe typically comprises a region of nucleotide sequence that hybridizes to at least about 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 consecutive nucleotides of a target nucleic acid. The target nucleic acid can be a sense strand of one of the target nucleic acid sequences, an anti-sense sequence, or naturally occurring mutants thereof. Preferably, the nucleic acid target is an mRNA.

Probes based on the nucleotide sequences can be used to detect or amplify transcripts or genomic sequences encoding the same or homologous proteins. In other embodiments, the probe further comprises a label group attached thereto, e.g., the label group can be a radioisotope, an enzyme, or an enzyme co-factor. Such probes can be used as a part of a genomic marker test kit for identifying cells which express a particular protein, such as by measuring a level of the protein-encoding nucleic acid in a sample of cells, e.g., detecting the target nucleic acid mRNA levels or determining whether the gene encoding the mRNA has been mutated or deleted.

In an additional preferred embodiment, an isolated nucleic acid molecule of the invention comprises a nucleic acid probe sequence that hybridizes, e.g., hybridizes under stringent conditions, to a target nucleotide sequence of interest. These hybridization conditions include washing with a solution having a salt concentration of about 0.02 molar at pH 7 at about 60° C. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, John Wiley & Sons, N.Y. (1989) 6.3.1–6.3.6. A preferred, non-limiting example of stringent hybridization conditions are hybridization in 6X sodium chloride/sodium citrate (SSC) at about 45° C., followed by one or more washes in 0.2 X SSC, 0.1% SDS at 50–65° C. As used herein, a "naturally-occurring" nucleic acid molecule refers to an RNA or DNA molecule having a nucleotide sequence that occurs in nature (e.g., encodes a natural protein).

The nucleic acid probes of the invention can be DNA or RNA or chimeric mixtures or derivatives or modified versions thereof, so long as it is still capable of hybridizing to the desired target nucleic acid. In addition to being labeled with a resonance energy transfer moiety, the nucleic acid sequence can be modified at the base moiety, sugar moiety, or phosphate backbone, and may include other appending groups or labels, so long as it is still capable of priming the desired amplification reaction, or functioning as a blocking oligonucleotide, as the case may be.

For example, a nucleic acid probe of the present invention can be chemically synthesized using naturally occurring nucleotides or variously modified nucleotides designed to increase the biological stability of the molecules or to increase the physical stability of the duplex formed between the complimentary nucleic acids, e.g., phosphorothioate derivatives and acridine substituted nucleotides can be used. A preferred example of a class of modified nucleotides which can be used to generate the nucleic acid probes is a 2'-O-methyl nucleotide. Additional examples of modified nucleotides which can be used to generate the nucleic acid probes include for example 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2 -thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the nucleic acid probe of the present invention comprises at least one modified sugar moiety selected from the group including but not limited to arabinose, 2-fluoroarabinose, xylulose, and hexose. In yet another embodiment, the nucleic acid probe of the present invention comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof. As stated above, a preferred example of a modified nucleotide which can be used to generate the nucleic acid probes is a 2'-O-methyl nucleotide.

Nucleic acid probes of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

Once the desired oligonucleotide is synthesized, it is cleaved from the solid support on which it was synthesized and treated, by methods known in the art, to remove any protecting groups present. The oligonucleotide may then be purified by any method known in the art, including extraction and gel purification. The concentration and purity of the oligonucleotide may be determined by examining oligonucleotide that has been separated on an acrylamide gel, or by measuring the optical density at 260 rn in a spectrophotometer.

Nucleic acid probes of the invention may be labeled with donor and acceptor moieties during chemical synthesis or the label may be attached after synthesis by methods known in the art. In a specific embodiment, the following donor and acceptor pairs are used: a luminescent lanthanide chelate, e.g., terbium chelate or lanthanide chelate, is used as the donor, and an organic dye such as fluorescein, rhodamine or CY-5, is used as the acceptor. Preferably, terbium is used as a donor and fluorescein or rhodamine as an acceptor, or europium is used as a donor and CY-5 as an acceptor. In another specific embodiment, the donor is fluorescent, e.g. fluorescein, rhodamine or CY-5, and the acceptor is luminescent, e.g. a lanthanide chelate. In yet another embodiment, the energy donor is luminescent, e.g., a lanthanide chelate, and the energy acceptor may be non-fluorescent.

In another specific embodiment, the donor moiety is a fluorophore. In another specific embodiment, both donor and acceptor moieties are fluorophores. Suitable moieties that can be selected as donor or acceptors in FRET pairs are set below:
4-acetamido-4'-isothiocyanatostilbene-2,2'disulfonic acid
acridine and derivatives:
  acridine
  acridine isothiocyanate
5-(2'-aminoethyl)aminonaphthalene-1-sulfonic acid (EDANS)
4-amino-N-[3-vinylsulfonyl)phenyl]naphthalimide-3,5disulfonate(LuciferYellow VS)
N-(4-anilino-1-naphthyl)maleimide
Anthranilamide
Brilliant Yellow
coumarin and derivatives:
  coumarin
  7-amino-4-methylcoumarin (AMC, Coumarin 120)
  7-amino-4-trifluoromethylcoumarin (Coumarin 151)
cyanosine
4'-6-diaminidino-2-phenylindole (DAPI)
5',5"-dibromopyrogallol-sulfonephthalein (Bromopyrogallol Red)
7-diethylamino-3-(4'-isothiocyanatophenyl)-4-methylcoumarin
diethylenetriamine pentaacetate
4-(4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansyl chloride)
4-(4'-dimethylaminophenylazo)benzoic acid (DABCYL)
4-dimethylaminophenylazophenyl-4'-isothiocyanate (DABITC)
eosin and derivatives:
  eosin
  eosin isothiocyanate
erythrosin and derivatives:
  erythrosin B
  erythrosin isothiocyanate
  ethidium
fluorescein and derivatives:
  5-carboxyfluorescein (FAM)
  5-(4,6-dichlorotriazin-2-yl)aminofluorescein (DTAF)
  2'7'-dimethoxy-4'5'-dichloro-6-carboxyfluorescein (JOE)
  fluorescein
  fluorescein isothiocyanate
  QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:
  pyrene
  pyrene butyrate
  succinimidyl 1-pyrene butyrate
Reactive Red 4 (Cibacron® Brilliant Red 3B-A)
rhodamine and derivatives:
  6-carboxy-X-rhodamine (ROX)
  6-carboxyrhodamine (R6G)
  lissamine rhodamine B sulfonyl chloride
  rhodamine (Rhod)
  rhodamine B
  rhodamine 123
  rhodamine X isothiocyanate
  sulforhodamine B
  sulforhodamine 101
  sulfonyl chloride derivative of sulforhodamine 101 (Texas Red)
  N,N,N',N'-tetramethyl-6-carboxyrhodamine (TAMRA)
  tetramethyl rhodamine
  tetramethyl rhodamine isothiocyanate (TRITC)
riboflavin
rosolic acid
terbium chelate derivatives One of ordinary skill in the art can easily determine, using art-known techniques of spectrophotometry, which fluorophores will make suitable donor-acceptor FRET pairs. For example, FAM (which has an emission maximum of 525 nm) is a suitable donor for TAMRA, ROX, and R6G (all of which have an excitation maximum of 514 nm) in a FRET pair. Probes are preferably modified during synthesis, such that a modified T-base is introduced into a designated position by the use of Amino-Modifier C6 dT (Glen Research), and a primary amino group is incorporated on the modified T-base, as described by Ju et al. (1995, Proc. Natl. Acad. Sci. USA 92:4347–4351). These modifications may be used for subsequent incorporation of fluorescent dyes into designated positions of the nucleic acid probes of the present invention.

The optimal distance between the donor and acceptor moieties will be that distance wherein the emissions of the donor moiety are maximally absorbed by the acceptor moiety. This optimal distance varies with the specific moieties used, and may be easily determined by one of ordinary skill in the art using well-known techniques. For energy transfer in which it is desired that the acceptor moiety be a fluorophore that emits energy to be detected, the donor and acceptor fluorophores are preferably separated when hybridized to target nucleic acid by a distance of up to 30 nucleotides, more preferably from 1–20 nucleotides, and still more preferably from 2 to 10 nucleotides and more preferably separated by 3, 4, 5, 6, 7, 8 and 9 nucleotides. For energy transfer wherein it is desired that the acceptor moiety quench the emissions of the donor, the donor and acceptor moieties are preferably separated by a distance of less than 10, 9, 8, 7, 6, 5, 4, 3, 2, or 1 nucleotide (e.g., on the opposite strand, complementary nucleotides of a duplex structure), although a 5 nucleotide distance (one helical turn) is also advantageous for use.

In yet another embodiment, the nucleic acid probes of the invention may be further labeled with any other art-known detectable marker, including radioactive labels such as $^{32}P$, $^{35}S$, $^{3}H$, and the like, or with enzymatic markers that produce detectable signals when a particular chemical reaction is conducted, such as alkaline phosphatase or horseradish peroxidase. Such enzymatic markers are preferably heat stable, so as to survive the denaturing steps of the amplification process. Nucleic acid probes may also be indirectly labeled by incorporating a nucleotide linked covalently to a hapten or to a molecule such as biotin, to which a labeled avidin molecule may be bound, or digoxygenin, to which a labeled anti-digoxygenin antibody may be bound. Nucleic acid probes may be supplementally labeled during chemical synthesis or the supplemental label may be attached after synthesis by methods known in the art.

The nucleic acid probes of the invention have use in nucleic acid detection, or amplification reactions as primers, or in the case of triamplification, blocking oligonucleotides, to detect or measure a nucleic acid product of the amplification, thereby detecting or measuring a target nucleic acid in a sample that is complementary to a 3' primer sequence. Accordingly, the nucleic acid probes of the invention can be used in methods of diagnosis, wherein a sequence is complementary to a sequence (e.g., genomic) of an infectious disease agent, e.g. of human disease including but not limited to viruses, bacteria, parasites, and fungi, thereby diagnosing the presence of the infectious agent in a sample of nucleic acid from a patient. The target nucleic acid can be genomic or cDNA or mRNA or synthetic, human or animal, or of a microorganism, etc.

In one embodiment the inventor provides a useful screening tool for drug discovery where a rapid specific and sensitive assay can detect in vivo changes in the expansion role of protein transcripts of interest, either at a steady state or in response to the administration of drug candidates. In another embodiment that can be used in the diagnosis or prognosis of a disease or disorder, the target sequence is a naturally occurring or wild type human genomic or RNA or cDNA sequence, mutation of which is implicated in the presence of a human disease or disorder, or alternatively, the target sequence can be the mutated sequence. In such an embodiment, optionally, the amplification reaction can be repeated for the same sample with different sets of probes that amplify, respectively, the naturally occurring sequence or the mutated version. By way of example, the mutation can be an insertion, substitution, and/or deletion of one or more nucleotides, or a translocation.

EXAMPLES

Example 1

Dual Nucleic Acid Probes

Oligonucleotide Synthesis. Oligonucleotide probes and targets were synthesized using standard phosphoramidite chemistry on an Applied Biosystems model 394 automated DNA synthesizer (Foster City, Calif.). Molecular beacons were purified using dual reverse phase (RIP) plus ion-exchange (IE) high performance liquid chromatography (HPLC) on a Waters Model 600E HPLC system (Millipore Corp., Milford, Mass.). For RP-HPLC purification, oligonucleotides were loaded on a Hamilton PRP-1 column and eluted with a linear 5% to 50% acetonitrile gradient in 0.1 M triethyl-ammonium acetate (TEAA) pH 7.2 over 40 minutes. The oligonucleotides were additionally purified by IE-HPLC using a Source™ column (Amersham Pharmacia Biotech, Piscataway, N.J.) and eluted with a linear 0% to 50% 1 M LiCl gradient in 0.1 M Tris pH 8.0 over 40 minutes. Unmodified (target) oligonucleotides were purified using polyacrylamide gel electrophoresis. All oligonucleotides were synthesized at Integrated DNA Technologies, Inc. (Coralville, Iowa).

Figure 2:
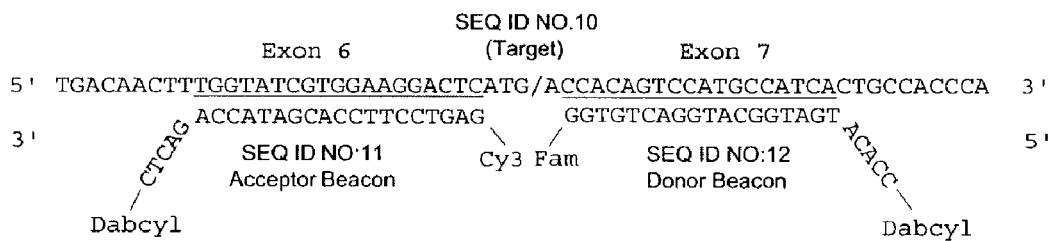
FIG. 2 shows a schematic of the assay system with 4-base spacing between donor and acceptor molecular beacons when hybridized to the synthetic target. In this example both beacons have a probe length of 19 bases and a stem length of 5 bases. The underscores indicate the 38-base sequence of the target complementary to the beacons. Note that for each beacon one arm of the stem is part of the probe sequence so that the movement of the dye molecules is restricted after hybridization.

Probe and Target Design. All oligonucleotide probes were designed to be complementary in antisense orientation to the human GAPDH gene, as illustrated in FIG. 2. Specifically, a dabcyl quencher was attached to the 5'-end and a 6-Fam fluorophore was attached to the 3'-end of donor molecular beacons; a dabcyl quencher was attached to the 3'-end and either a Cyanine 3 (Cy3), 6-carboxyrhodamine (ROX), or Texas Red fluorophore was attached to the 5'-end of acceptor molecular beacons. The stem sequence was designed to participate in both hairpin formation and target hybridization (Tsourkas et al., 2002b). This beacon design was chosen to help fix the relative distance between the donor and acceptor fluorophores and improve energy transfer efficiency. Both the donor and acceptor beacons were designed with a probe length of 18 bases and a stem length of 5 bases. The probe length is defined as the portion of the molecular beacon that is complementary to the target. The synthetic wild-type GAPDH target has 4-base gap between the donor dye and the acceptor dye. Gap spacing was adjusted to 3, 5, and 6 bases by either removing a guanine residue or adding 1 or 2 thymine residues, as shown in Table 1.

TABLE 1

Design of Probes and Target Oligonucleotides

| Name | Sequence (5'—3') | Note |
|---|---|---|
| Fam donor-MB[1] | Dabcyl-ccacaTGATGGCATGGACTGTGG-Fam<br>SEQ ID NO:1 | Probe18/Stem 5 |
| Tb donor probe | TGATGGCATGGACTGTGG-DTPA-cs124-(Tb)<br>SEQ ID NO:2 | Probe 18/Stem 0 |
| Cy3 acceptor-MB | Cy3-GAGTCCTTCCACGATACCgactc-Dabcyl<br>SEQ ID NO:3 | Probe 18/Stem 5 |
| ROX acceptor-MB | ROX-GAGTCCTTCCACGATACCgactc-Dabcyl<br>SEQ ID NO:4 | Probe 18/Stem 5 |
| Texas Red acceptor-MB | Texas Red-GAGTCCTTCCACGATACCgactc-Dabcyl<br>SEQ ID NO:5 | Probe 18/Stem 5 |
| Target[2] n − 1 | ACTTT<u>GGTATCGTGGAAGG</u>ACTCATA<u>CCACAGTCCATGCCATCA</u>CTGCC<br>SEQ ID NO:6 | 3 base gap |
| Target n (WT) | ACTTT<u>GGTATCGTGGAAGG</u>ACTCATGA<u>CCACAGTCCATGCCATCA</u>CTGCC<br>SEQ ID NO:7 | 4 base gap |
| Target n + 1 | ACTTT<u>GGTATCGTGGAAGG</u>ACTCATTGA<u>CCACAGTCCATGCCATCA</u>CTGCC<br>SEQ ID NO:8 | 5 base gap |

TABLE 1-continued

Design of Probes and Target Oligonucleotides

| Name | Sequence (5'–3') | Note |
|---|---|---|
| Target n + 2 | ACTTT<u>GGTATCGTGGAAGGACTC</u>ATTTGA<u>CCACAGTCCATGCCATCA</u>CTGCC<br>SEQ ID NO:9 | 6 base gap |

[1] MB = Molecular Beacon. Lower case = bases added to create stem domains. Upper case = probe-target hybridizing domains. Upper case bold = bases participating in both stem formation and target binding
[2] Underscore = 18 base sequence complememtary to MB target binding domains. n = 4 bases the wild-type gap size Lanthanide Chelate Synthesis. A linear oligonucleotide with a probe length of 18 bases was labeled at its 3'-end with a diethylenetriaminepentaacetic acid (DTPA) chelate covalently joined to a sensitizer, cs124 (Cooper and Sammes, 2000). As demonstrated in Table 1, the sequence of this linear probe was identical to the probe domain of the donor molecular beacons specific for exon 7 of the human GAPDH gene.

The lanthanide chelate was prepared by first dissolving DTPA (500 mg, 1.4 μmole) in 30 mL of DMF and 1 mL of triethylamine. Cs124 (240 mg, 1.4 μmole), dissolved in 4 mL of DMF, was then added dropwise and mixed for 30 minutes. To this mixture, 5 mL (75 μmole) of ethylenediamine (EDA) was added and stirred at room temperature for two hours. The mixture was then stored in the refrigerator overnight. A slightly off-white precipitate had formed and was centrifuged down further. The DMF supernatant was removed and the pellet was washed with isopropanol several times and then with ether resulting in a fine white powder, which was dried under a vacuum for 2 hours. The powder was resuspended in water and RP-HPLC purified using a Hamilton PRP-1 column. The sample was eluted with a linear 0% to 30% acetonitrile gradient in 0.1 M TEAA pH 7.2 over 20 minutes at a flow rate of 10 mL/min. The first peak was collected, and the DTPA-cs124 product was dried and reconstituted to a concentration of 15 mM in 0.1 M Borate Buffer, pH 8.5.

Disuccinimidyl suberate (1.84 mg, 5 μmoles; Pierce Chemical) was dissolved in 100 μL of DMSO and added to 0.1 μmoles of oligonucleotides with a 3'-amine, dissolved in 100 uL of DMSO. The mixture was incubated at 40° C. for 2 hours. The oligonucleotides were then acetone precipitated and reconstituted in 100 μl of 0.1 M sodium borate pH 8.5. 50 uL of 15 mM DTPA-cs124-EDA product in borate buffer was added to the oligonucleotide solution and mixed overnight. Oligonucleotide-DTPA-csl24-EDA conjugates were purified using reversed-phase (RP) HPLC. The oligonucleotides were loaded on a PRP-1 column and eluted with a linear 5% to 50% acetonitrile gradient in 0.1 M TEAA pH 7.2 over 40 minutes. The collected peak was lyophilized and reconstituted in $dH_2O$ at 5 μM. $TbCl_3$ (Terbium) dissolved in PBS was then added to the sample at a 10:1 molar ratio and incubated at room temperature for 30 minutes. The Europium chelates were synthesized following the same protocol.

Hybridization and Detection Assays. Hybridization experiments were conducted with 50 pmoles of donor beacon, 50 pmoles of acceptor beacon and 50 pmoles of complementary target in a total volume of 100 μL (0.5 μM). All experiments were conducted at 37° C. in HB buffer containing 10 mM KCl, 5 mM $MgCl_2$, and 10 mM Tris-HCl, pH 7.5, which was supplemented with 1% Bovine Albumin Serum to block non-specific interactions with the microplate. The samples were mixed and allowed to equilibrate at 37° C for 20 minutes before performing fluorometry. A Safire microplate fluorometer (Tecan, Zurich, Switzerland) was used to excite the donor beacons and detect resulting emission (500 nm to 650 nm) in FRET measurements. The excitation wavelength was varied from 395 nm to 495 nm to determine the wavelength that resulted in the maximal FRET between the donor and acceptor molecules. In a two-photon experimental set-up, the excitation spectra of Fam-and Cy3-labeled linear oligonucleotides were obtained. A tunable laser was adjusted to excite the samples at wavelengths ranging from 700 nm to 875 nm. The fluorescence emission between 505 nm and 555 nm was detected from the Fam sample and the emission between 590 and 650 nr was detected from the Cy3 sample using ultra-sensitive, low noise avalanche photodiodes.

For LRET measurements, the Terbium and Europium donor probes were excited at a wavelength of 325 nm, and the emission was recorded from 500 nm to 650 nm for assays with Terbium donors, and from 550 nm to 750 nm for assays involving Europium donors. The emission detection had a lag time of 50 μs with an integration time of 1 ms. The maximal excitation and emission wavelengths of the organic and lanthanide dyes used in this study are summarized in Table 2.

TABLE 2

Maximal Excitation and Emission Wavelengths of Organic and Lanthanide Dyes

| Dye Molecule | Excitation (nm) | Emission (nm) | Extinction Coefficient ($M^{-1} cm^{-1}$) | Note |
|---|---|---|---|---|
| 6-Fam | 494 | 518 | 83,000 | Donor |
| Terbium Chelate | 300–340 | 546 | 10,000–35,000 | Donor |
| Europium Chelate | 300–340 | 620 | 10,000–35,000 | Donor |
| Cy3 | 552 | 570 | 150,000 | Acceptor |
| Rox | 585 | 605 | 82,000 | Acceptor |
| Taxes Red | 583 | 603 | 116,000 | Acceptor |

FRET of Organic Dye Pairs. A series of solution-phase assays were conducted to determine whether the signal generated by a pair of molecular beacons hybridized to the same target oligonucleotide can be differentiated from the signal due to false-positive events. For organic dye pairs, the same donor beacon (i.e., a molecular beacon with a fluorescent donor dye) was tested with three acceptor (reporter) beacons for the magnitudes of background signal and positive (FRET) signal. Here, "background" is defined as fluorescence detected from one or both beacons in the absence of target or from either beacon alone in the presence of target. Thus background represents any fluorescence emission detected in the absence of a FRET event due to the simultaneous hybridization of the donor and acceptor beacons to the same target. If fluorescence excitation is limited to wavelengths $\lambda_e$ optimal for the donor fluorophore and signal detection is limited to wavelengths $\lambda_d$ optimal for the acceptor (reporter) fluorophore, fluorescent signal should be low unless both beacons hybridize to the same target and FRET occurs. However, since fluorescence from organic fluorophores occurs over a broad range of wavelengths, it is possible for fluorescence emission from the donor at $\lambda_d$ and from the acceptor due to direct excitation at $\lambda_e$ to contribute to background. "Positive signal" is defined as FRET-induced fluorescence detected when both beacons are bound to the same target, again restricting excitation to wavelengths $\lambda_e$ and limiting detection to wavelengths $X_d$.

As illustrated in Table 1, the donor molecular beacon was labeled with 6-Faam on the 3'-end, and the acceptor molecular beacons were labeled with Cy3, ROX, or Texas Red on the 5'-end. Sequences of donor and acceptor molecular beacons were chosen to be complementary to adjacent sites within exon 6 and exon 7 of the human GAPDH gene and were positioned with a four base separation between donor and acceptor fluorophores when wild-type target was used. Four types of assays were performed with each donor/acceptor beacon pair: (1) both donor and acceptor beacons in the absence of target, with a typical emission spectrum (i.e., fluorescence intensity as a function of wavelength) shown as curve a in FIG. 3 (spectrum a); (2) donor beacon only in the presence of target, with a typical emission spectrum shown as curve b in FIG. 3 (spectrum b); (3) acceptor beacon only in the presence of target, with a typical emission spectrum shown as curve c in FIG. 3 (spectrum c); and (4) both donor and acceptor beacons in the presence of target, with a typical emission spectrum shown as curve d in FIG. 3 (spectrum d). Assays (2) and (3) simulate the limiting false positive scenario where most of the molecular beacons open as a result of nuclease degradation, denaturation, or non-specific protein interactions (which hereafter will collectively be referred to as 'degraded' beacons).

Figure 3:
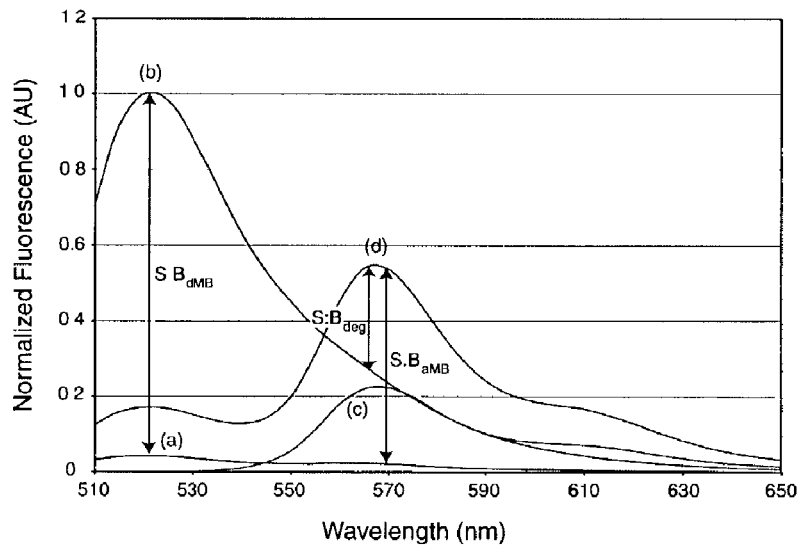
FIG. 3 shows typical emission spectra of dual FRET molecular beacons. Three signal-to-background ratios are defined: S:B$_{dMB}$ represents the enhancement in fluorescence of a conventional molecular beacon in the presence of target. S:B$_{aMB}$ indicates the increase in fluorescence resulting from the sensitized emission of the acceptor. S:N$_{deg}$ is the ratio of the signal from sensitized emission of the acceptor to the false-positive signal.

To illustrate the advantages of using duel FRET molecular beacons and to compare the performance of different acceptor molecular beacons, several signal-to-background ratios were calculated. As illustrated in FIG. 3, the first is S:BdMB, the ratio of the peak fluorescence intensity of emission spectrum b defined above for donor molecular beacons (dMB) to that of emission spectrum a at the same wavelength. Although spectrum a was generated with both the donor and acceptor beacons in solution, the fluorescence signal is largely due to the donor beacons, for the emission of the acceptor beacons at the corresponding wavelength is almost zero, as can be seen from curve c in FIG. 3. Thus, $S:B_{dMB}$ represents the signal-to-background ratio of the conventional single molecular beacon assay. The second is S:BaMB, the ratio of the peak fluorescence intensity of emission spectrum d of the acceptor molecular beacon (aMB) due to FRET to that of emission spectrum a at the same wavelength. Clearly, $S:B_{aMB}$ represents the signal-to-background ratio of the dual FRET molecular beacons assay without degraded beacons. The third one, $S:B_{deg}$, is defined as the ratio of the peak fluorescence intensity of emission spectrum d due to FRET to that of emission spectrum b or c at the same wavelength, whichever is higher. $S:B_{deg}$ represents the signal-to-background ratio of the dual FRET molecular beacons assay for the limiting case that most of the donor and acceptor beacons are being degraded. Here we assume that, with up to $1 \times 10^5$ molecular beacons per cell, the probability of having both degraded donor and acceptor beacons at the same spatial location (i.e., within a cylinder of 0.2 μm in diameter and 1 μm in thickness) in a fluorescence imaging assay is small. This is especially true considering that, with chemical modifications of the beacon backbone, only a small fraction (<50%) of the molecular beacons would be degraded in an intracellular environment. It is worth mentioning that all the signal-to-background ratios discussed above change with the donor excitation wavelength.

Figure 4A:
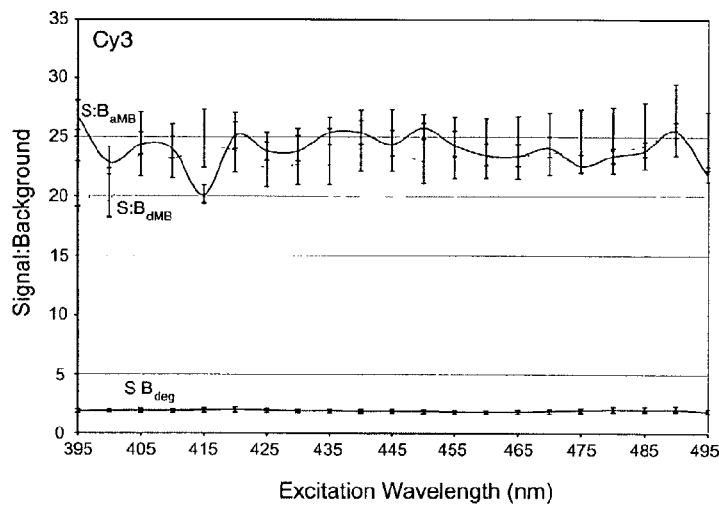
FIGS. 4a–4c show signal-to-noise ratios for dual FRET molecular beacons with (4a) a Fam-Cy3 FRET pair, (4b) a Fam-ROX FRET pair and (4c) a Fam-Texas Red FRET pair. The error bars display the minimum and maximum ratios calculated for dual FRET molecular beacons separated by 3, 4, 5, or 6 bases.

As shown in FIG. 4a, $S:B_{aMB}$ of the FRET assay with Cy3-labeled acceptor beacons was almost identical to $S:B_{dMB}$ of the donor beacon alone over the entire range of excitation wavelengths tested. Neither parameter varied significantly, ranging between 20 and 25, as the excitation wavelength $\lambda$ was increased. The dual FRET molecular beacons, however, did generate a signal 2 to 3 times stronger compared with that of degraded beacons, i.e., $S:B_{deg}$ has a value of 2–3, while conventional molecular beacons cannot differentiate between signals due to degraded and hybridized probes. Signal enhancement upon molecular beacon/target binding is strongly affected by cation concentration and temperature. In this case, the $S:B_{deg}$ was relatively low since the assay temperature of 37° C. was near the stem melting temperature.

Figure 4B:
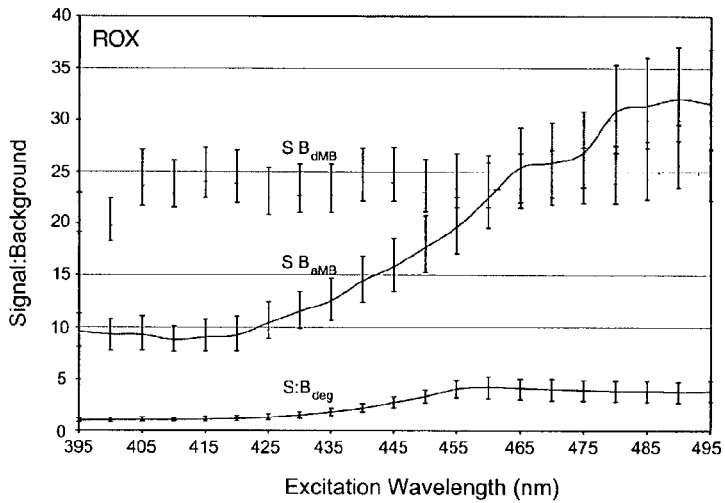

When a ROX fluorophore was used as the acceptor dye, $S:B_{aMB}$ was found to be ~10, about half of $S:B_{dMB}$, at low excitation wavelengths $\lambda$ (e.g., 395 nm to 425 nm), as shown in FIG. 4b. However, when $\lambda$ was increased, $S:B_{aMB}$ also increased. In fact, when $\lambda$ became larger than 460 nm, $S:B_{aMB}$ was higher than $S:B_{dMB}$, reaching values above 30. This indicates that the dual FRET molecular beacons with a Fam-ROX FRET pair can perform better than the conventional molecular beacons even in the absence of beacon degradation issues. The value of $S:B_{deg}$ also increased with increasing $\lambda$, reaching values close to 5 at $\lambda$=455 nm, remaining between 4 and 5 for wavelengths ranging from 455 nm to 495 nm.

Figure 4C:
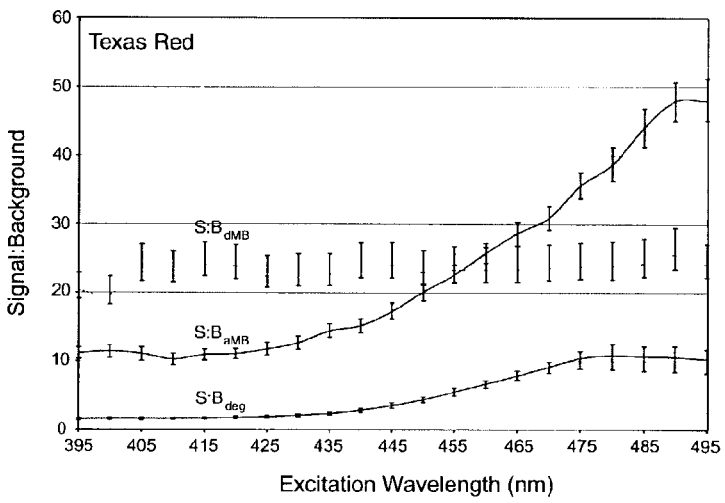
Figure 5:
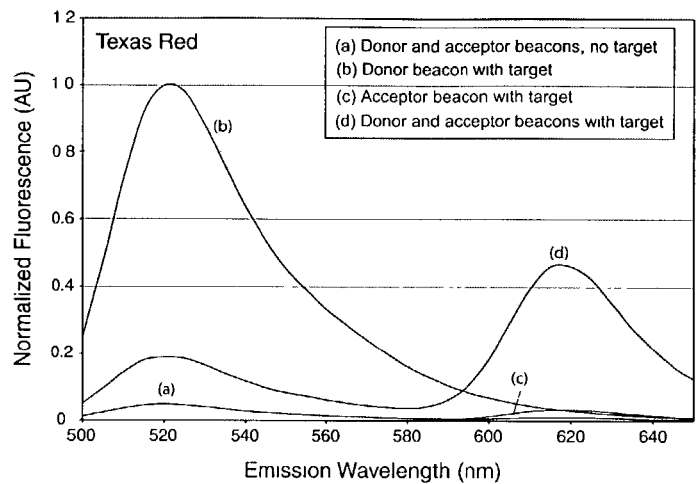
FIG. 5 shows emission spectra for dual FRET molecular beacons with a Fam-Texas Red FRET pair. The samples described in the figure were excited at a wavelength of 475 nm.

Acceptor beacons labeled with Texas Red were found to perform the best among the three acceptor dyes considered. Value of $S:B_{aMB}$ increased from 10 to nearly 50 as $\lambda$ was increased from 395 nm to 495 nm. Moreover, as $\lambda$ was increased from 455 mn to 475 nm the value of $S:B_{deg}$ increased from ~2 to over 10 and remained around 10 for $\lambda$>475 nm, as demonstrated in FIG. 4c. Therefore, the signal generated by binding of both donor and acceptor beacons to a target could be 10 times brighter than false-positive signals. An example of the spectra generated using the Fam-Texas Red FRET pair is given in FIG. 5.

Figure 6:
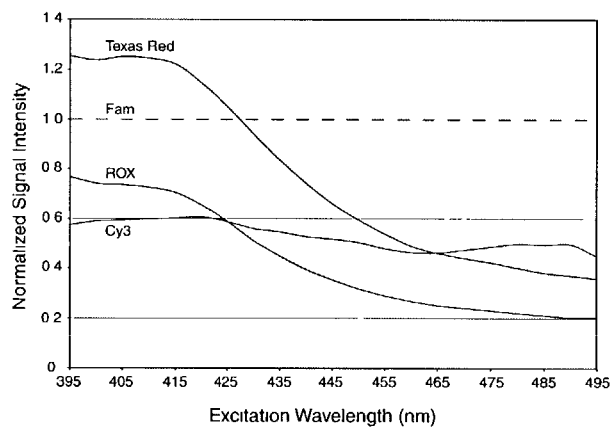
FIG. 6 shows normalized peak emission of the acceptor due to FRET for molecular beacon pairs with a Fam donor and a Cy3, ROX, or Texas Red acceptor. All the intensities were normalized relative to the peak intensity of the Fam-labeled donor beacon bound to target.

Although the performance of dual FRET molecular beacons is better than non-FRET molecular beacons due to increased signal-to-background ratio and the ability to differentiate between bound and degraded molecular beacons, the peak fluorescence intensity of the acceptor beacons was typically lower than that of the Fam-labeled donor beacons, as shown in FIG. 6. Specifically, at wavelengths where optimal FRET signal-to-background ratios were obtained, for Fam-Texas Red FRET pair the peak signal intensity of the acceptor was only about 40% of that emitted by the Fam-donor alone, and only about 25% for the Fam-ROX FRET pair, which may limit ultimate sensitivity.

Figure 7:
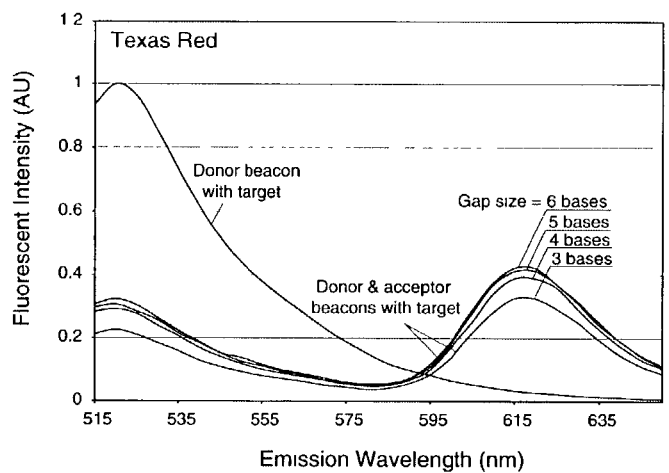
FIG. 7 shows the effect of spacing between donor and acceptor beacons on the fluorescence emission of acceptor dye for dual FRET molecular beacons with a Fam donor and a Texas Red acceptor. Four different targets were tested, separating the donor and acceptor beacons by 3, 4, 5, or 6 bases.

The efficiency E of fluorescence resonance energy transfer between thea donor and acceptor fluorophores varies according to $$E = 1/(1 + R^6/R_0^6) \qquad (1)$$

where R is the distance between donor and acceptor dyes, and $R_0$ is the Förster energy transfer distance or the distance at which E=0.5. For typical fluorophores $R_0$=1~5 nm. Equation (1) implies that the gap (i.e., the number of bases) between the donor and acceptor beacons should be kept small. However, too small a gap size may result in steric interference between fluorophores or might lead to other interaction between donor and acceptor (such as ground state quenching), which is unfavorable. The gap size can influence the relative orientation of the fluorophores, also affecting energy transfer efficiency. A gap size of 8 bases was found to be optimal for energy transfer in the single-stranded random-coil conformation (Ju et al., 1995; Hung et al., 1997). Further, base composition can influence fluorescence efficiency. The combination of a fluorescein dye attached to a guanine base can decrease peak fluorescence intensity by as much as 30% (M. Behlke, unpublished observation). To optimize design parameters, hybridization experiments were conducted using targets that separate the donor and acceptor beacons by 3, 4, 5, and 6 bases. The nucleotides closest to the probe-binding region were identical for each target sequences. When the distance between the donor and acceptor beacons was increased from 3 to 6 bases, there was a slight increase in the FRET signal intensity, as demonstrated by the curves displayed in FIG. 7. This trend was found to be the same for all the acceptor fluorophores studied.

LRET of Lanthanide Dyes. Conventional organic dyes used for FRET assays are limited by problems associated with the overlapping of donor/acceptor excitation and emission spectra. To dramatically improve the signal-to-background ratio, the inventor takes advantage of the sharp emission peaks and the long lifetime of a lanthanide chelate (Li and Selvin, 1997; Cooper and Sammes, 2000). Specifically, a lanthanide donor is substituted for the Fam donor and modified the detection system to employ time-resolved spectroscopy. The lanthanide donor was a linear oligonucleotide probe labeled at its 3'-end with the Terbium chelate DTPA-cs124 (Table 1). The same series of acceptor molecular beacons were tested as before, including beacons with Cy3, ROX, or Texas Red fluorophores. Note that the use of lanthanide donor allows for shorter wavelength excitation, as demonstrated in Table 2.

Figure 8A:
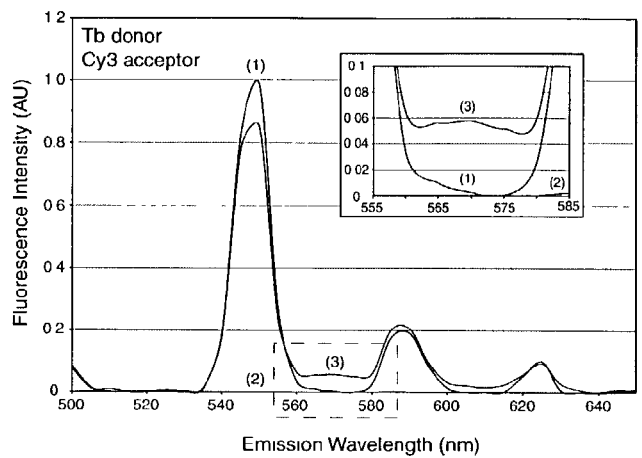
FIGS. 8a and 8b show time resolved emission spectra obtained in a two-probe detection assay using Terbium chelate as a donor and (8a) Cy3 as an acceptor and (8b) ROX as an acceptor. All samples were excited at a wavelength of 325 nm.
Figure 8B:
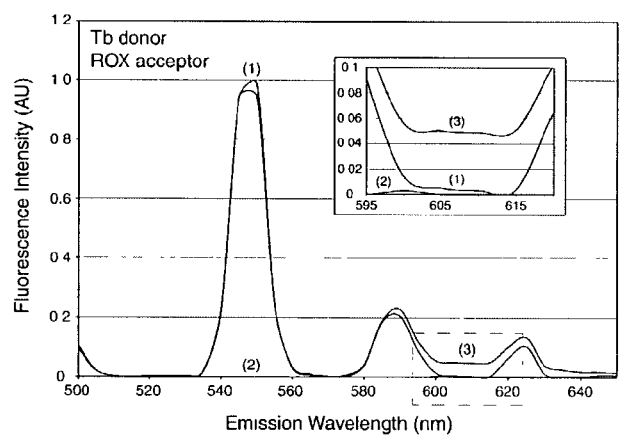

The results of LRET experiments with a lanthanide donor are shown in FIGS. 8a, b. As shown by curve (1) in FIG. 8a, at 325 nm excitation, when the Terbium-chelate labeled donor probes bound to Cy3 labeled acceptor beacons, they exhibited several sharp emission peaks separated by valleys with fluorescence intensity close to zero; while the fluorescence emission from acceptor molecular beacons alone hybridized to targets was extremely low, as shown by curve (2). With binding of both donor probes with Terbium-chelate and acceptor molecular beacons to target, a sensitized emission of the acceptor due to LRET was observed, shown as curve (3). As clearly demonstrated by the insert in FIG. 8a, at emission wavelengths where background from the lanthanide donor was near zero, extremely high signal-to-background ratios were observed. For Cy3-labeled acceptor beacon, the optimal detection wavelength is around 573 nm. Similar features were exhibited in FIG. 8b in which the time resolved emission spectra obtained with 325 nm excitation in a dual LRET probe assay using Terbium chelate as a donor and ROX as an acceptor were displayed. It is again very clear that at certain emission wavelengths the signal-to-background ratio approaches infinity. As seen from the insert of FIG. 8b, for ROX-labeled acceptor beacon, the optimal detection wavelength is around 614 nm. Although the fluorescence emission due to energy transfer was very low, these results nevertheless suggest that there is a significant potential for use of lanthanide donors with dual energy transfer molecular beacons.

To determine the possible detrimental effect of small gap size between donor and acceptor probes on LRET, the spacing between the Terbium-labeled donor probe and the Cy3 or ROX-labeled acceptor beacon was varied from 3 to 9 bases. It was found that the detected fluorescence intensity is not sensitive to the gap spacings tested, i.e., with a spacing of 3, 4, 5, 6 and 9 bases, the signal levels were similar (data not shown), suggesting that the possible detrimental effect was negligible when both probes hybridized to the target with a relatively small gap spacing. Using Equation (1), it is readily shown that, with the gap spacing varying from 3 to 9 bases, the energy transfer efficiency does not change much, since the Forster distance $R_0$ for the Terbium/Cy3 LRET pair is large (6.12 nm) (Selvin, 2002). For example, when R in Equation (1) increases from 1 nm (~3 bases) to 2 nm (~6 bases) and to 3 nm (~9 bases), the energy transfer efficiency E only decreases by 0.12% and 1.37%, respectively.

Figure 9:
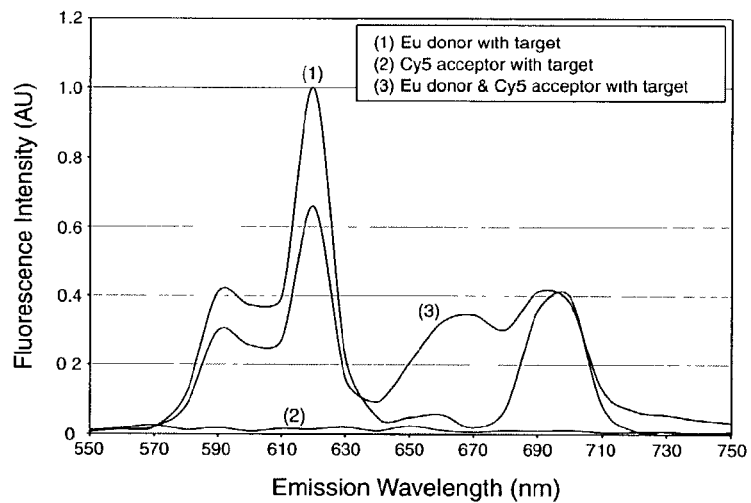
FIG. 9 shows time resolved emission spectra generated by a two-probe detection assay utilizing a Europium-labeled oligonucleotide as a donor probe and a Cy5-labeled oligonucleotide as an acceptor probe.

Due to the narrow emission peaks exhibited by lanthanide dyes, and the use of time-resolved fluorescence detection, it is not necessary to include a quencher molecule in the acceptor molecular beacons, although the stem-loop hairpin structure of the beacon may still be beneficial. However, when the detection of point mutations is not involved, the use of linear LRET pairs of oligonucleotide probes is attractive owing to its potential in reducing cost while having comparable performance. To demonstrate the concept, donor oligonucleotide probes labeled with a Europium chelate at its 3'-end, and acceptor oligonucleotide probes labeled at its 5'-end with a Cy5 fluorophore were synthesized, and in-solution hybridization and time-resolved emission detection assays were performed. The resulting emission spectra are displayed in FIG. 9. Similar to the results obtained using Terbium-chelate donors, at 325 nm excitation, the emission spectrum of Europium donor bound to target showed several peaks within the range of 550 nm to 750 nm, as demonstrated by curve (1). The fluorescence emission of the Cy5-labled acceptor probe due to probe/target hybridization is again almost zero (curve (2)). When both donor and acceptor probes hybridized to the same target, there was a sensitized emission of the acceptor due to LRET, as shown by curve (3). Evidently, at certain wavelengths (such as 670 nm), the background signal due to degraded donor and acceptor probes becomes very low, leading to a high signal-to-background ratio. It was found that with the DTPA-cs124 chelate used in this study, the LRET probe pairs with a Terbium donor performs better than the LRET probe pair with a Europium donor and a Cy5 acceptor.

Although conventional molecular beacons can in theory detect mRNA transcripts in living cells, conditions within the intracellular environment can limit their utility in cellular imaging of gene expression. Specifically, molecular beacons bound to target mRNAs cannot be distinguished from those degraded by nucleases, or destabilized due to interactions with proteins. Here we report a dual molecular beacon method that combines the advantages of molecular beacons with two-probe resonance-energy transfer methods. Conventional and time-resolved fluorescence spectroscopy studies indicate that dual FRET molecular beacon pairs are capable of distinguishing between bound and degraded beacons with improved signal to background than previous methods. Moreover, with a lanthanide chelate as the donor dye, the signal-to-background ratio can be extremely high at certain wavelengths.

These features are especially important in the detection and quantification of gene expression in living cells where false-positive signals due to probe degradation and interaction with DNA binding proteins must be distinguished from the 'true' signal that results from probe/target binding. We envision widespread applications of the dual energy transfer molecular beacon methods in laboratory and clinical studies of gene expression in living cells, tissues and even animals using single- or multi-photon microscopy, time-resolved fluorescence microscopy, and fluorescence endoscopy. For example, it is plausible to use this methodology for the specific and sensitive detection of the expression of oncogenes and tumor-suppresser genes in living cells, potentially making it a very simple and effective clinical tool for the early detection and diagnosis of malignancy.

When using the dual LRET molecular beacons for gene detection and quantification examples of chelates that can be employed include DTPA-cs124, BCPDA (4,7-bis(chlorosulfophenyl)-1,10-phenanthroline-2,9-dicarboxylic acid) and BHHCT (4,4-bis(1,1,1,2,2,3,3-heptafluoro-4,6-hexanedion-6-yl)-chlorosulfo-o-terphenyl (Evangelista et al., 1988; Lopez et al., 1993; Yuan et al., 1998; Sueda et al., 2000; Cooper and Sammes, 2000).

Figure 10A:
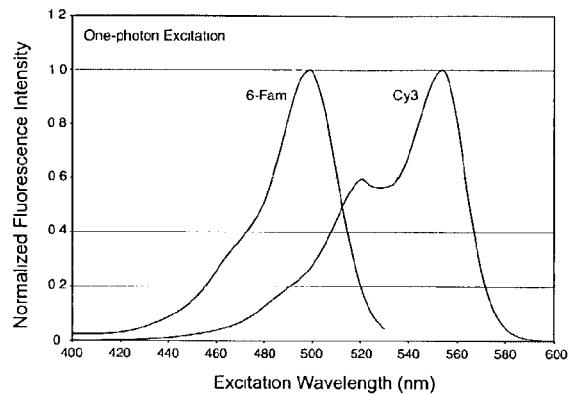
FIGS. 10a and 10b show one-photon (10a) and two-photon (10b) excitation spectra of 6-Fam labeled and Cy3 labeled oligonucleotides.

Another improvement is to use two photon excitation instead of one-photon excitation. So far, all the dual FRET beacon/target hybridization assays performed were based on a one-photon excitation source (Xenon flash lamp). However, because of the overlapping excitation-emission spectrums of the organic donor and acceptor molecules for FRET, it is often difficult to excite the donor without also directly exciting the acceptor. For example, as demonstrated in FIG. 10a, the maximum excitation of a donor Fam molecule occurs at ~500 nm, but at the same wavelength an acceptor Cy3 molecule is also excited to 25% of its maximum. Therefore, if an acceptor beacon is degraded by nucleases and the fluorophore is separated from the dabcyl quencher it will be excited, giving a false-positive signal. Ideally, free acceptor fluorophores should be minimally excited by the excitation source and the only ones that are excited would be those due to FRET when both the donor and acceptor beacon are bound to the same target.

Figure 10B:
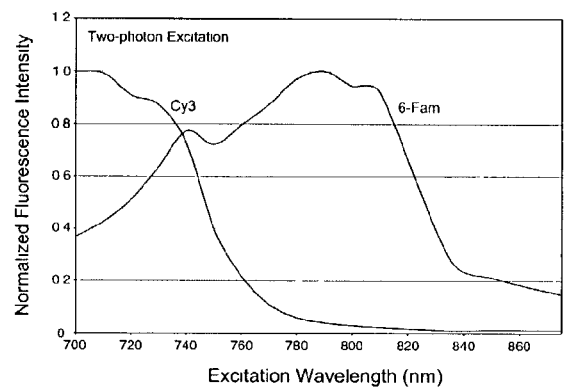

One strategy to minimize the direct excitation of the acceptor fluorophore is to use a two-photon excitation source. Two-photon excitation cross-sections of fluorophores do not necessarily follow the same trends as one-photon excitation spectrums. For example, as shown in FIG. 10b, although the maximum excitation of Cy3 occurs at higher wavelengths than Fam when one-photon excitation is used, with two-photon excitation the Cy3 fluorophore is actually excited at lower wavelengths. Further, when a donor Fam molecule is maximally excited at ~790 nm, the Cy3 acceptor is only excited about 4% of its maximum. This alone is more than a 6-fold reduction in the direct excitation of the Cy3 acceptor compared with one-photon excitation. Two-photon excitation also has the advantage of reduced photo-bleaching, reduced background fluorescence from scattering, and the ability to penetrate deeper into biological tissue than one-photon excitation. Therefore, two-photon excitation is potentially a powerful approach in dual FRET molecular beacon studies.

Example 2

Shared Stem Nucleic Acid Probes

Oligonucleotide Synthesis. Oligonucleotide probes and targets were synthesized using standard phosphoramidite chemistry on an Applied Biosystems model 394 automated DNA synthesizer (Foster City, Calif.). Molecular beacons were purified using a 2-step reverse phase (RP) plus ion-exchange (IE) high performance liquid chromatography (HPLC) on a Waters Model 600E HPLC system (Millipore Corp., Milford, Mass.). For RP-HPLC purification, oligonucleotides were loaded on a Hamilton PRP-1 column and eluted with a linear 5% to 50% acetonitrile gradient in 0.1 M triethyl-ammonium acetate (TEAA) pH 7.2 over 40 minutes. The oligonucleotides were additionally purified by IE-HPLC using a Source™ column (Amersham Pharmacia Biotech, Piscataway, N.J.) and eluted with a linear 0% to 50% 1 M LiCl gradient in 0.1 M Tris pH 8.0 over 40 minutes. Unmodified (target) oligonucleotides were purified using polyacrylamide gel electrophoresis. All oligonucleotides were synthesized at Integrated DNA Technologies, Inc. (Coralville, Iowa).

Figure 12:
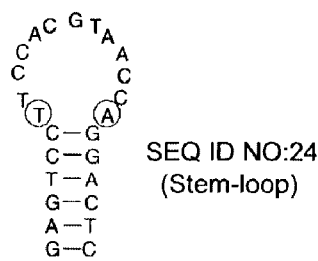
FIGS. 12a and 12b show examples of the design constraint of shared-stem molecular beacons with certain stem/probe combinations.
Figure 12:
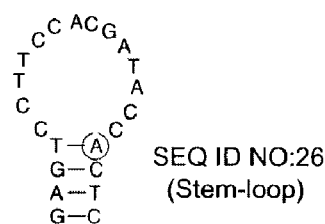

Molecular Beacon Design. Two types of molecular beacons were designed and synthesized; both contain target-specific probe sequence complementary in antisense orientation to exon 6 of the human GAPDH gene, a Cy3 fluorophore at the 5'-end, and a dabcyl quencher at the 3'-end. As illustrated in FIG. 11a, one type follows the conventional design of molecular beacons in that the target-specific probe domain was centrally positioned between two complementary arms that form the stem; the sequence of these arms were independent of the target sequence. Shared-stem molecular beacons, on the other hand, were designed to have one arm of the stem complementary to the target sequence, as shown schematically in FIG. 11b. In both cases, the probe length $L_p$ is defined as the portion of the molecular beacon that is complementary to the target, and the stem length $L_s$ is the number of bases of each complementary arm. All the molecular beacons had $L_p$=19 bases (see Table 3). Conventional molecular beacons were synthesized with $L_s$=4, 5 and 6 bases. The shared-stem molecular beacons were synthesized with $L_s$=4, 5 and 7 bases. As illustrated by FIG. 12a, a 6-base stem may not be synthesized because the shared-stem molecular beacon sequence is constrained, i.e., part of the arm sequence that makes up the 6-base stem is predetermined since the 5'-end of the shared-stem molecular beacon must complement the target sequence and the 3'-stem is created solely to complement the 5'-stem sequence. This inadvertently forces an additional base pairing in the stem. It should be noted that the stem sequence of a shared-stem molecular beacon is not adjustable since one arm of the stem is designed to complement the target. This limitation often precludes the design of certain stem/probe length combinations, as demonstrated in FIG. 12b for a molecular beacon with a probe length of 18 bases and a stem length of 4 bases. Five target oligonucleotides were also synthesized, one wild-type and four with mismatches at assorted locations, as shown in Table 3.

TABLE 3

The Design of Probes and Target Oligonucleotides

| Name | Sequence (5'–3') | Notes |
|---|---|---|
| Shared-stem 19/4 | Cy3-GAGTCCTTCCACGATACCActc-Dabcyl<br>SEQ ID NO:13 | Probe 19/Stem 4 |
| Shared-stem 19/5 | Cy3-GAGTCCTTCCACGATACCAgactc-Dabcyl<br>SEQ ID NO:14 | Probe 19/Stem 5 |
| Shared-stem 19/7 | Cy3-GAGTCCTTCCACGATACCAggactc-Dabcyl<br>SEQ ID NO:15 | Probe 19/Stem 7 |
| Conventional 19/4 | Cy3-aatcGAGTCCTTCCACGATACCAgagg-Dabcyl<br>SEQ ID NO:16 | Probe 19/Stem 4 |
| Conventional 19/5 | Cy3-ctgacGAGTCCTTCCACGATACCAgtcag-Dabcyl<br>SEQ ID NO:17 | Probe 19/Stem 5 |
| Conventional 19/6 | Cy3-ctgagcGAGTCCTTCCACGATACCAgctca-Dabcyl<br>SEQ ID NO:18 | Probe 19/Stem 6 |
| Target WT | ACTTTGGTATCGTGGAAGGACTCATGA<br>SEQ ID NO:19 | Perfect match |
| Target A | ACTTTGGTATCGTGGAAGGAaTCATGA<br>SEQ ID NO:20 | Single mismatch |
| Target B | ACTTTGGTATCGTaGAAGGACTCATGA<br>SEQ ID NO:21 | Single mismatch |
| Target C | ACTTTGGTATCGTaGAAGGAaTCATGA<br>SEQ ID NO:22 | Double mismatch |
| Target D | ACTTGGTATCGTaaAAGGACTCATGA<br>SEQ ID NO:23 | Double mismatch |

(1) Molecular Beacons: Lower case = bases added to create stem domains. Upper case = probe-target hybridizing domains. Upper case bold = bases participating in both stem formation and target binding
(2) Targets: Underscore = 19 base sequence complememtary to beacons. Lower case bold = mismatch bases in targets Equilibrium Analysis. Molecular beacons in the presence of target were assumed to exist in three phases: 1) as duplex with target, 2) as stem-loop hairpin, and 3) in random coil conformation. Dissociation constants describing the transition between these phases were determined by analyzing the thermal denaturation profile of molecular beacons in the presence and absence of target (Bonnet et al., 1999). Denaturation profiles were obtained by recording the fluorescence intensity of a 50 μL solution containing 200 nM of molecular beacon in the presence of 0 to 20 μM of target at temperatures ranging from 5° C. to 95° C. Specifically, the temperature of the hybridization solution was brought to 95° C. and reduced by 1° C. increments to 5° C. The temperature was then raised with 1° C. increments back to 95° C. to ensure that the solution reached equilibrium and no hysteresis had occurred. The temperature was held at each temperature increment for ten minutes and fluorescence was measured for the final 30 seconds. The fluorescence intensity of each test solution was adjusted to correct for the intrinsic variance of fluorescence over temperature. Each thermal denaturation assay was performed in hybridization buffer containing 10 mM Tris, 50 mM KCl, and 5 mM $MgCl_2$.

The fluorescence intensity data describing the thermal denaturation profile of each molecular beacon and molecular beacon-target duplex was used to determine the respective dissociation constant as described in Bonnet et al. 1999. Specifically, dissociation constants $K_{12}$ characterizing the transition between phase 1 (bound to target) and phase 2 (closed beacon) of molecular beacons were obtained for all beacon-target pairs and for all molecular beacons in the absence of target. Further, the dissociation constants $K_{12}$ were used to determine the changes in enthalpy ($\Delta H_{12}$) and entropy ($\Delta S_{12}$) associated with each beacon-target duplex. The errors calculated for the thermodynamic parameters signify a 95% confidence interval.

Molecular Beacon Specificity. The fraction of molecular beacons bound to target, α, was calculated for each molecular beacon-target pair as a function of temperature. All calculations utilized the thermodynamic parameters, enthalpy change $\Delta H_{12}$ and entropy change $\Delta S_{12}$, obtained from the thermal denaturation profiles for each beacon-target duplex $$\frac{\alpha}{(1-\alpha)(\eta-\alpha)\hat{B}_0} = e^{(-\Delta H_{12}/R\theta)+(\Delta S_{12}/R)} \qquad (2)$$

where θ is the temperature in Kelvin, R is the gas constant, $\eta = T_0/B_0$, $\hat{B}_0 = B_0 c_0$, $T_0$ and $B_0$ are respectively initial concentration of target and beacons, and $c_0$ is the unit concentration 1M (Ratilainen et al., 1998). The value of α was calculated for each molecular beacon-target pair as a function of temperature for samples containing $B_0=200$ nM of molecular beacon and $T_0=400$ nM of target. The melting temperature $\theta_m$ is defined as the temperature at which half of the molecular beacons are bound to target, i.e., α=0.5.

Kinetic Analysis. A SPEX fluorolog-2 spectrofluorometer with an SFA-20 rapid kinetics stopped-flow accessory and a temperature/trigger module (SFA-12) was used to measure molecular beacon-target binding kinetics. Specifically, the fluorescence intensity emitted from a rapidly mixed solution containing 250 nM molecular beacons and 2.5 µM targets was recorded over time for each molecular beacon-target pair. The hybridization reaction was assumed to obey the second order reaction kinetics $$B + T \underset{k_2}{\overset{k_1}{\rightleftharpoons}} D, \quad \frac{d[D]}{dt} = k_1[B][T] - k_2[D] \tag{3}$$

where [B], [T] and [D] are the concentrations of unbound molecular beacon, unbound target, and molecular beacon-target duplex, respectively; $k_1$ is the on-rate and $k_2$ the off-rate of molecular beacon-target hybridization. The exact solution of Equation 3 gives $$1 - \frac{[D(t)]}{[D_{eq}]} = e^{-\Delta k_1 t}\left[1 - \lambda \left[D(t)\frac{1}{[D_{eq}]}\right]\right] \tag{4}$$

where $\Delta=\sqrt{(B_0+T_0+K_{12})^2-4B_0T_0}$, $[D_{eq}]=(B_0+T_0+K_{12}-\Delta)/2$, $\lambda=[D_{eq}]^2/B_0T_0$, and $K_{12}=k_2/k_1$ is the dissociation constant discussed above. Since the concentration of molecular beacon-target duplex is unknown at any given time, it was assumed that $(F(t)-F_o)/(F_{eq}-F_o)=[D(t)]/[D_{eq}]$ where $F(t)$ is the fluorescence intensity at time t, $F_o$ is the initial fluorescence intensity, and $F_{eq}$ is the fluorescence intensity as $t \to \infty$. In order to obtain the on-rate $k_1$ based on the fluorescence measurement, two different curve-fitting schemes were used. The first utilized a least-square method by fitting a straight line to a logarithmic form of Equation 4, $$\frac{1}{\Delta}\ln\left(1 - \frac{\{F(t) - F_o\}}{\{F_{eq} - F_o\}}\right) = \frac{1}{\Delta}\ln\left(1 - \lambda\frac{\{F(t) - F_o\}}{\{F_{eq} - F_o\}}\right) - k_1 t \tag{5}$$

with a slope equal to $k_1$. Alternatively, a non-linear least-square method was used to determine the value of $k_1$ from Equation 4 directly. The results obtained using these two approaches were compared.

Figure 13:
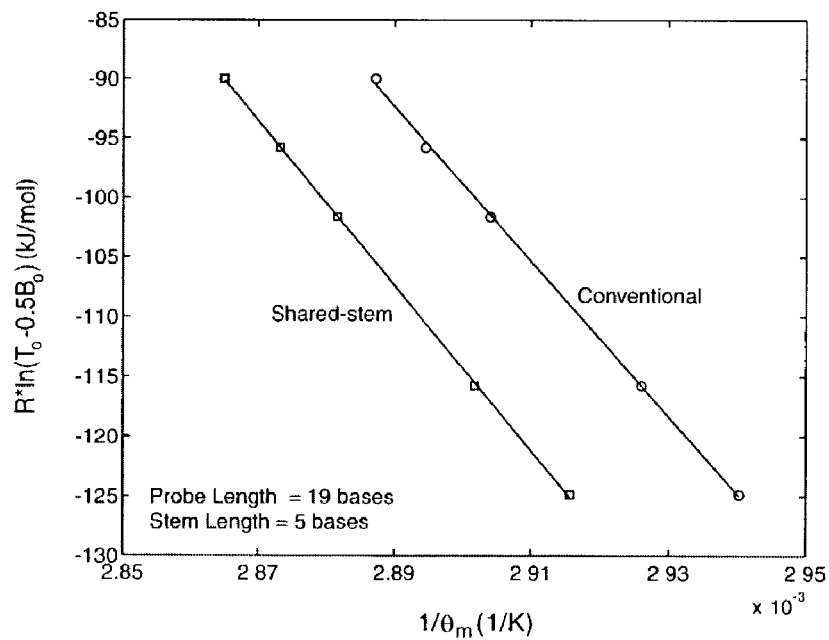
FIG. 13 shows a comparison of the milting temperature of shared-stem and conventional molecular beacons as determined by the initial concentrations of probe and target. By fitting the data with a straight line, changes in enthalpy (slope of the fitted line) and entropy (y-intercept) characterizing the phase transition between bound-to-target and stem-loop conformations of a molecular beacon were obtained.

Thermal Analysis. To better understand how the performance of shared-stem molecular beacons differ from that of the conventional molecular beacons, thermodynamic parameters of these two types of molecular beacon were obtained and compared. In particular, the enthalpy and entropy changes $\Delta H_{12}$ and $\Delta S_{12}$ describing the phase transition between bound-to-target and stem-loop conformations were determined for conventional and shared-stem molecular beacons using van't Hoff plots. As demonstrated in FIG. 13, these plots display the inverse of melting temperature $1/\theta_m$ as determined by $R \ln(T_0-0.5B_0)$ shown as the ordinate. Since at melting temperature, $$R\ln(T_0 - 0.5B_0) = -\Delta H_{12}\frac{1}{\theta_m} + \Delta S_{12} \tag{6}$$

the slope of the fitted straight line of each curve in FIG. 13 represents the enthalpy change—$\Delta H_{12}$ and the y-intercept represents the entropy change $\Delta S_{12}$. It was found that in general, the shared-stem molecular beacons have a higher melting temperature, i.e., they form more stable probe/target duplexes than conventional molecular beacons. The changes of enthalpy and entropy for all the molecular beacon-target combinations tested are summarized in Table 4.

TABLE 4

Changes in Enthalpy and Entropy of Conventional and Shared-stem Molecular Beacons in the Presence of Target

| Target | Probe Length | Stem Length | Conventional Molecular Beacons | | Shared-stem Molecular Beacons | | |
|---|---|---|---|---|---|---|---|
| | | | −ΔH (kJ/mol) | ΔS (kJ/mol · K) | Stem Length | −ΔH (kJ/mol) | ΔS (kJ/mol · K) |
| WT | 19 | 4 | 823 ± 168 | 2281 ± 489 | 4 | 862 ± 116 | 2383 ± 336 |
| A | 19 | 4 | 577 ± 62 | 1595 ± 184 | 4 | 708 ± 36 | 1967 ± 106 |
| B | 19 | 4 | 527 ± 27 | 1471 ± 79 | 4 | 586 ± 54 | 1628 ± 161 |
| C | 19 | 4 | 472 ± 23 | 1336 ± 70 | 4 | 478 ± 49 | 1340 ± 148 |
| D | 19 | 4 | 480 ± 38 | 1352 ± 115 | 4 | 521 ± 87 | 1461 ± 262 |
| WT | 19 | 5 | 649 ± 28 | 1784 ± 83 | 5 | 690 ± 16 | 1887 ± 46 |
| A | 19 | 5 | 418 ± 23 | 1133 ± 70 | 5 | 446 ± 20 | 1205 ± 59 |
| B | 19 | 5 | 385 ± 24 | 1055 ± 73 | 5 | 391 ± 24 | 1057 ± 72 |
| C | 19 | 5 | 324 ± 17 | 901 ± 54 | 5 | 369 ± 57 | 1025 ± 175 |
| D | 19 | 5 | 291 ± 25 | 790 ± 76 | 5 | 319 ± 28 | 861 ± 85 |
| WT | 19 | 6 | 467 ± 16 | 1265 ± 48 | 7 | 413 ± 10 | 1096 ± 28 |
| A | 19 | 6 | 404 ± 25 | 1105 ± 76 | 7 | 370 ± 13 | 998 ± 38 |
| B | 19 | 6 | 380 ± 26 | 1055 ± 79 | 7 | 351 ± 39 | 956 ± 117 |
| C | 19 | 6 | 367 ± 19 | 1058 ± 61 | 7 | 260 ± 30 | 707 ± 93 |
| D | 19 | 6 | 373 ± 29 | 1065 ± 91 | 7 | 245 ± 25 | 653 ± 79 |

To minimize the number of independent variables involved in controlling probe/target hybridization, all the molecular beacons were designed to have identical probe sequences. Further, for molecular beacons with a stem length of 5 bases and a probe length of 19 bases, the stem sequence of the conventional molecular beacons was chosen such that energetically the stem was similar to that of the shared-stem molecular beacons. The free energy changes were calculated using nearest neighbor approximations (Zucker 2000).

Figure 14:
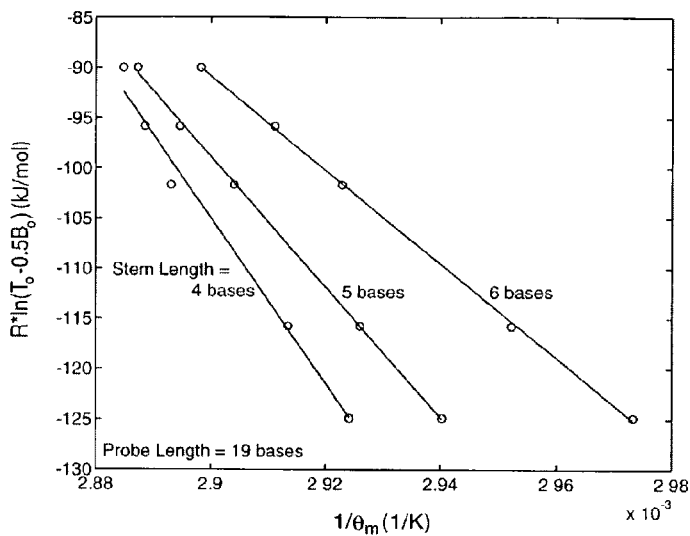
FIG. 14 shows determination of the changes in enthalpy (slope of the fitted line) and entropy (y-intercept) characterizing the phase transition between bound-to-target and stem-loop conformations for conventional molecular beacons. Similar trend was found for shared-stem molecular beacons.

The difference in thermodynamic behavior between conventional and shared-stem molecular beacons can be understood in terms of the ability of the flanking arms to interact with each other. With shared-stem molecular beacons, once part of the stem (one arm) is bound to the target, it is less likely to interact with its complementary arm, resulting in a more stable probe/target duplex. In contrast, the arms of a conventional molecular beacon do not bind to the target and are thus more likely to interact with each other as driven by thermal energy, increasing the tendency of forming a closed molecular beacon by dissociating from the target. Not surprisingly, the stem length of a molecular beacon influenced the equilibrium state of both the shared-stem and conventional beacons in the presence of target. As shown in FIG. 14, as the stem length was increased from 4 to 6 bases, conventional molecular beacons were found to dissociate from target molecules more readily. A very similar trend was true for shared-stem molecular beacons (data not shown). This indicates that hybridization is less favorable for molecular beacons with longer stems.

Figure 15A:
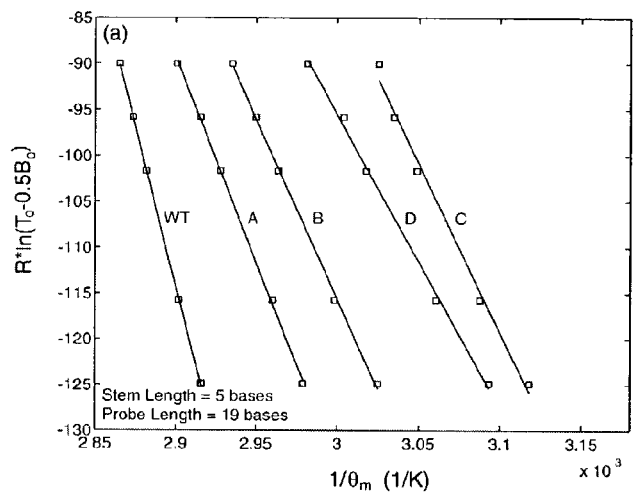
FIGS. 15a and 15b show determination of the changes in enthalpy (slope of the fitted line) and entropy (y-intercept) characterizing the phase transition between bound-to-target and stem-loop conformations for FIG. 15a shared-stem and FIG. 15b conventional molecular beacons interacting with wild-type and mutant targets.

The changes in enthalpy and entropy that control the dissociation of conventional and shared-stem molecular beacons from targets with mismatches were also determined (see Table 4). It was found that shared-stem molecular beacons formed more stable duplexes with each of the target molecules tested. However, as displayed in FIG. 15, when point mutations were present in the target oligonucleotide, both types of molecular beacons dissociated from their targets more readily. The magnitude of change depended on both the number of mismatches and their location. Compared with the wild-type target, a point mutation near the center of the probe-binding domain (Target B) was found to have a larger effect on molecular beacon dissociation than a mutation near the end of the probe-binding domain (Target A). As expected, two point mutations (Targets C and D) on a target had a more profound effect on the dissociation of molecular beacons from targets than that with one point mutation.

Melting Temperature. To further elucidate the effect of molecular beacon structure on the stability of the probe-target duplex, the melting temperatures $\theta_m$ for conventional and shared-stem molecular beacons with a probe length of 19 bases and stem lengths ranging from 4 to 7 bases were compared, as shown in FIG. 6. It was found that conventional molecular beacons had lower melting temperatures than shared-stem molecular beacons for each of the stem lengths considered; however, both types of molecular beacons exhibited similar trends. Specifically, the melting temperature progressively decreased as the stem length increased. In fact, it appears that the melting temperature would be quite low for conventional molecular beacons with a probe length of 19 bases and a stem length of 7 bases or greater. This is because that with long free arms of the stem a bound molecular beacon is very easy to dissociate from the target and form a stable hairpin structure even at low temperatures.

Figure 15B:
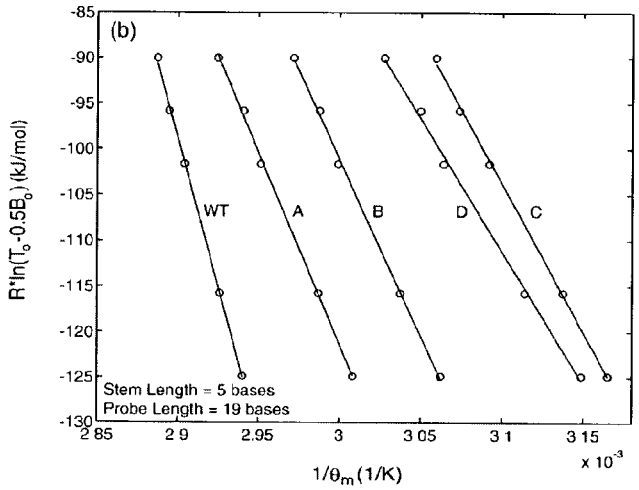
Figure 16:
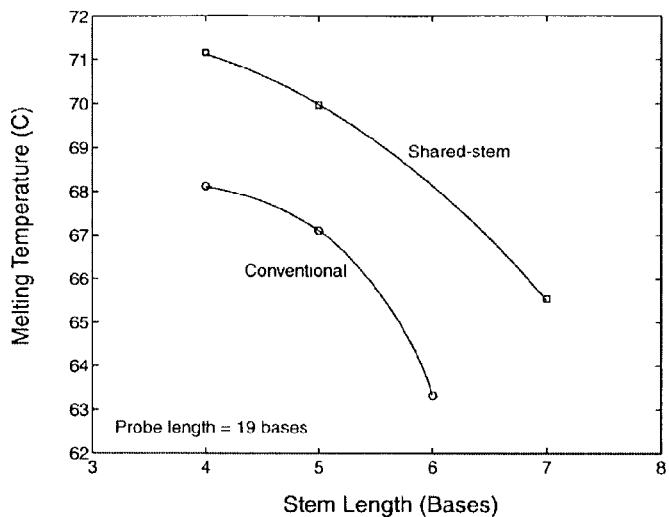
FIG. 16 shows a comparison of melting temperatures as a function of stem length for conventional and hared-stem molecular beacons in the presence of wild-type target.
Figure 17A:
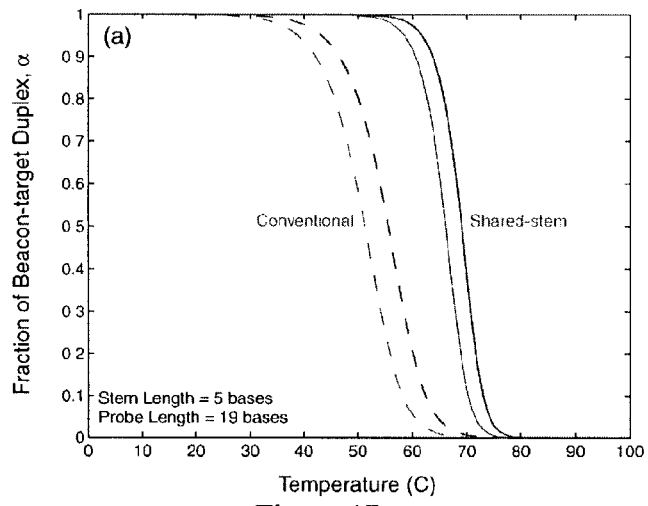
FIGS. 17a and 17b show melting behavior of conventional and shared-stem molecular beacons with a 19-base probe and a 5-base stem.
Figure 17B:
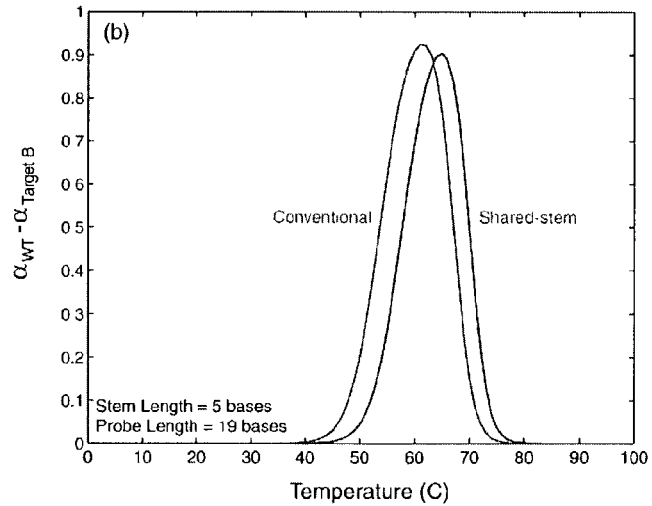

Molecular Beacon Specificity. Melting curves that display the fraction of molecular beacons in duplex form, $\alpha$, as a function of temperature were obtained for each molecular beacon and probe-target pair. As demonstrated in FIG. 17a, the difference in melting temperature $\theta_m$ (i.e., temperature at $\alpha=0.5$) between beacon/wild-type-target and beacon/mutant-target duplexes was found to be slightly larger for conventional molecular beacons compared with corresponding shared-stem molecular beacons. Further, the difference in the fraction of molecular beacons bound to wild-type target and mutant target, $\alpha_{WT}-\alpha_{Target\ B}$, as a function of temperature was found to be similar for conventional and shared-stem molecular beacons, although the maximum value of $\alpha_{WT}-\alpha_{Target\ B}$ is slightly higher for the former, as shown in FIG. 15b. The conventional molecular beacons was also found to maintain a value of $\alpha_{WT}-\alpha_{Target\ B}>0$ over a slightly broader range of temperatures than shared-stem molecular beacons, but again the different is very small. This implies that the conventional molecular beacons may exhibit only a slightly higher specificity than shared-stem molecular beacons.

Figure 18:
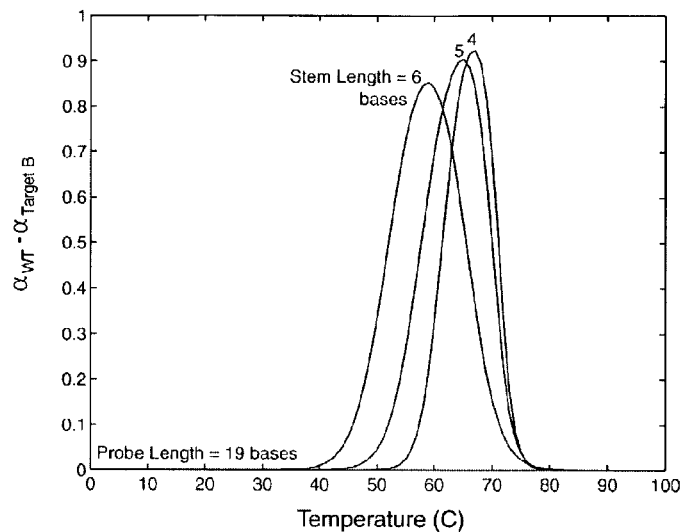
FIG. 18 shows the difference in the fraction of beacons bound to wild-type and mutant targets for shared-stem molecular beacons with stem lengths of 4, 5, and 6 bases. The same trend is true for conventional molecular beacons.

The effect of stem length on molecular beacon specificity was also found to be similar for conventional and shared-stem molecular beacons. Specifically, the curves in FIG. 18 demonstrate that, as the stem length is increased the heightened competition between a unimolecular reaction and bimolecular hybridization broadens the transition between bound and unbound states. This results in an improved ability to discriminate between targets over a wider range of temperature but lowers the maximum difference in the fraction of beacons bound to wild-type and mutant targets.

Figure 19A:
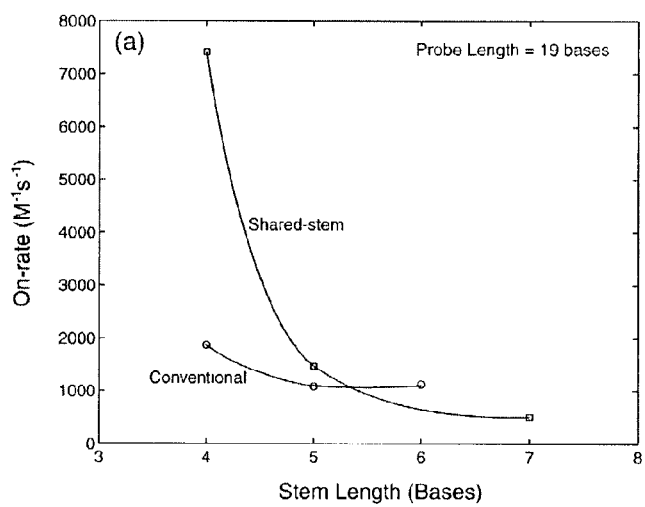
FIGS. 19a and 19b show a comparison between conventional and shared-stem molecular beacons on FIG. 19a the on-rate of hybridization with target and FIG. 19b the dissociation constant without target (i.e., the transition between stem-loop hairpin and random-coiled beacons) for molecular beacons with a 19-base probe length and various stem lengths.
Figure 19B:
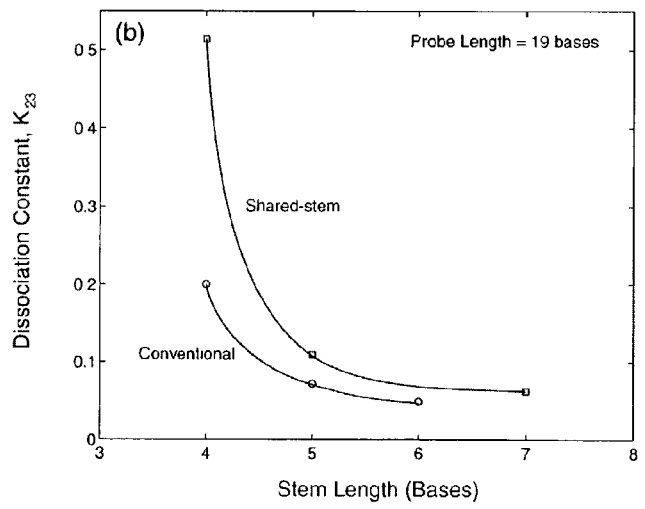

Kinetic Analysis. The on-rate of shared-stem and conventional molecular beacons hybridized to wild-type target as a function of stem length is displayed in FIG. 19a. It is seen that for shared-stem molecular beacons, an increase in stem length from 4 to 5 bases induced a 5-fold reduction in its on-rate, which was further reduced by 3-fold when the stem length was increased from 5 to 7 bases. In contrast, the on-rate of conventional molecular beacons only decreased slightly when the stem length was increased from 4 to 6 bases. It is interesting to note that, with stem lengths of 5 bases or larger, the shared-stem and conventional molecular beacons have on-rates differing only by less than a factor of 2. However, the shared-stem molecular beacons with a 4-base stem hybridized to wild-type targets four times faster than the corresponding conventional molecular beacons. This large difference in the rate of hybridization most likely resulted from the variations in the stability of the hairpin structure. To further illustrate, the dissociation constants $K_{23}$ of the conventional and shared-stem molecular beacons in the absence of target are shown in FIG. 19b. Interestingly, there seems to be a clear correlation between the on-rate of beacon hybridization and the stability of the stem-loop structure. This is understandable since $K_{23}$ represents the transition from hairpin (phase 2) to random coiled (phase 3) conformations of molecular beacons, and a higher $K_{23}$ implies that the molecular beacons are easier to open.

Molecular beacons have become a very useful tool for many homogeneous single-stranded nucleic acid detection assays due to their ability to differentiate between bound and unbound states and their improved specificity over linear probes. However, to optimize the performance of molecular beacons for different applications, it is necessary to understand their structure-function relationships. Here is described a new design of molecular beacons, i.e., the shared-stem molecular beacons, of which the stem-arm nearest the reporter dye participates in both hairpin formation and target hybridization. In contrast to conventional molecular beacons whose stems are independent of the target sequence and thus can freely rotate around the probe-target duplex, this new design helps immobilize the fluorophores of molecular beacons when they hybridize to the target, which is desirable when two molecular beacons are used in a fluorescence resonance energy transfer (FRET) assay (Tsourkas and Bao 2001). Specifically, with shared-stem molecular beacons, there is a better control of the distance between the donor dye on one beacon and the acceptor dye on the other beacon, since the rotational motion of the fluorophore-attached stem-arm is constrained, as illustrated in FIG. 11b. To facilitate the design and application of, and to reveal the differences between, shared-stem and conventional molecular beacons, we performed a systematic study of the thermodynamic and kinetic parameters that control the hybridization of these molecular beacons with complementary and mismatched targets.

In general, it was found that compared with shared-stem molecular beacons, conventional molecular beacons form less stable duplexes with single-stranded nucleic acid targets but have a slightly improved ability to discriminate between wild-type and mutant targets. The difference in the duplex stability can be explained by the thermal-driven interactions between the two stem-forming arms after the molecular beacon hybridized to a target molecule. Unlike linear oligonucleotide probes, a molecular beacon can have two stable conformations: bound to target, and as a stem-loop hairpin. These two stable states compete with each other, giving rise to an improved specificity. The additional freedom inherent in both arms of conventional molecular beacon increases the likelihood that, driven by thermal fluctuations, these arms will encounter with each other, allowing the molecular beacon to dissociate from the target with a higher probability. This reduced stability also corresponds to a smaller value in the free energy difference between bound and unbound states of the probe-target duplex. The change in free energy due to any mismatch between the probe and target, therefore, will have a more profound effect on the preference of the stem-loop hairpin conformation of the conventional molecular beacons, leading to an improved ability to differentiate between wild-type and mutated targets. However, this improvement was found to be marginal.

With any given probe length and sequence, the hybridization kinetics of molecular beacons appears to be primarily dependent on the length and sequence of the stem, regardless of whether they are designed in the conventional or shared-stem configuration. Both types of molecular beacons exhibited comparable hybridization rates when the dissociation constants describing the thermal fluctuation induced opening of the stem-loop structure, $K_{23}$, were similar. When the difference in $K_{23}$ for the shared-stem and conventional molecular beacons was increased, so was the difference in the hybridization on-rate.

In addition to the above-mentioned differences in the behavior of shared-stem and conventional molecular beacons, the choice of the stem length is independent of the probe length for conventional molecular beacons, whereas there are certain constraints on the stem-length and probe-length combinations in designing the share-stem molecular beacons. This, together with the dependence of the thermodynamic and kinetic properties on the probe and stem lengths demonstrated in this study, should be considered in the design of molecular beacons for specific applications.

Example 3

K-ras and Survivin Detection

It is well established that cancer cells develop due to genetic alterations in oncogenes and tumor suppressor genes and abnormalities in gene expression that provide growth advantage and metastatic potential to the cells. A critical step in diagnosing and treating cancer in its early stages is to detect cancer cells based on the genetic alterations. An important example is pancreatic cancer, the fifth most fatal cancer in the US. Only 12% of patients diagnosed with pancreatic cancer can survive for one year; the 5-year overall survival rate is approximately 3–5%. The main reason for the poor prognosis of pancreatic cancer is that very few of these cancers can be found early. Current clinical diagnostic procedures such as CT-scan and endoscopic retrograde cholangiopancreatography (ERCP) have a low sensitivity in detecting pancreatic tumors less than 2 cm in size. In spite of the extensive biomedical research efforts during the last few decades, over 90% of the patients with pancreatic cancer have already undergone local and/or distant metastases by the time of diagnosis, often making it too late to cure. Therefore, it is extremely important to detect pancreatic cancer in its early stages based on molecular markers rather than the size of the tumor.

A novel way of achieving early detection of cancer is to identify cancer cells through detection of mRNA transcripts that exist in cancer cells but not in normal cells. Here is demonstrated the dual-FRET molecular beacons of the present invention for the early detection of cancer cells.

K-ras is one of the most frequently mutated genes in human cancers. A member of the G-protein family, K-ras is involved in transducing growth-promoting signals from the cell surface. Point mutations of K-ras are found in 80–100% of pancreatic, 40–60% of colon, and 25–50% of lung adenocarcinomas, suggesting that mutant K-ras is a sensitive marker for pancreatic cancer detection. Further, K-ras mutations occur almost exclusively in three hot spots (codons 12, 13 and 61). Most of them are concentrated at codon 12, which facilitates the design of molecular beacons. Since K-ras mutations occur very early in the development of pancreatic cancer, assays targeting K-ras mutations can lead to early detection of pancreatic carcinomas. Other oncogenes and tumor-suppressor genes involved in pancreatic cancer include p53, p16, MADH4, DPC4, BRCA2, MKK4, STK11, TGFBR1 and TGFBR2.

There is increasing evidence recently suggesting that survivin, one of the inhibitor of apoptosis proteins (LAPs), is a good tumor marker for several types of cancers. Survivin is normally expressed during fetal development but not in most normal adult tissues. However, high levels of survivin are detected in many human cancer types and transformed human cells. In particular, a recent study has demonstrated the presence of survivin in 77% (20 out of 26 cases) of pancreatic duct cell adenocarcinomas by immunohistochemistry, immunoblotting and RT-PCR assays. The results from this study also suggested that the expression of survivin is present in early stages of neoplastic transition in pancreatic cancer cells. However, expression of survivin was not detected in pancreatic tissues obtained from 5 normal persons and 12 patients with chronic pancreatitis, nor was it found in inflammatory cells around tumor cells. The absence of survivin expression in normal pancreas, pancreatic tissue of chronic pancreatitis patients and other normal tissues makes it an ideal molecular marker for the detection of pancreatic cancer cells. Although molecular beacons can be designed to target alterations of many oncogenes and tumor-suppressor genes, in the proposed study we opt to focus on the detection of K-ras mutations and the expression of survivin in pancreatic cells.

It has been shown that K-ras mutations can be detected in blood, pancreatic juice and pancreatic tissue samples of pancreatic cancer patients using DNA purification and mutant-enriched PCR followed by single strand conformation polymorphism (SSCP), restriction fragment-length polymorphisms (RELP), or allele-specific oligodeoxynucleotide hybridization (ASOH). Although identification of K-ras mutations by PCR is a fairly sensitive molecular approach, the procedures for PCR and subsequent assays are very time-consuming, making them difficult to become clinical procedures. Furthermore, detection of K-ras mutations in DNA from peripheral blood or pancreatic juice alone is not sufficient for diagnosis of pancreatic cancer since it lacks the specificity for the determination of the cellular origin of the K-ras mutation. A better way to detect pancreatic cancer is to use nucleic acid probes of the present invention to detect K-ras mutations in cancer cells directly. Utilization of prior nucleic acid probes to detect K-ras mutations in PCR products of DNA samples isolated from lung cancers has been reported and the specificity has been established. However, to date the use of nucleic acid probes for the detection of mutant K-ras mRNA in intact tumor cells has not been reported. One advantage of using the molecular beacons approach is that a cocktail of multiple such probes can be delivered into cells for different molecular markers of cancer.

An important issue in detecting K-ras mutations in cells is that as a signaling protein the expression level of K-ras mRNA may not be very high (<1,000 copies per cell), even in cancer cells. Further, the secondary structures of K-ras and survivin mRNAs may influence the binding between nucleic acid probes of the present invention and the targets. Thus, it is preferred to optimize the design of molecular beacons and the beacon delivery conditions so that high detection specificity and sensitivity can be achieved. By routinely combining the nucleic acid probes of the present invention approach with high-sensitivity fluorescence microscopy, it will likely be possible to detect as few as 10 copies of mRNA per cell.

To further examine probe-target hybridization and energy transfer between nucleic acid probes of the present invention, dual-FRET molecular beacons were designed and synthesized. Specifically, the molecular beacons were designed to target human GAPDH mRNA. The donor proes were synthesized with a 6-FAM donor fluorophore (D) at the 3' end and a Dabcyl quencher (Q) at the 5' end. Similarly, acceptor probes were synthesized with a Cy3 acceptor fluorophore (A) at the 5' end and a Dabcyl quencher (Q) at the 3' end (see Table 5 below). The donor and acceptor beacons are chosen such that they are complementary to part of the target sequence. The loop portion, therefore, is 13 bases in length. The synthetic targets mimicking the GAPDH IVT RNA exon 6/exon 7 junction are designed so that the gap between the two beacons hybridizing on the same target is respectively 3, 4, 5 or 6 bases, with 4-base gap being that of the wild-type. All the nucleic acid probes of the present invention were synthesized at Integrated DNA Technologies (IDT, Inc).

As illustrated above, thermodynamics and binding kinetics of molecular interactions underlies the design of the nucleic acid probes of the present invention. The free energy difference between keeping the stem-loop structure and forming the probe-target duplex is the main driving force for hybridization. The nucleic acid probes of the present invention can have three different phases in solution: hairpin, random coil, and probe-target duplex. The relative portions of these phases depend on the structure of the probe, probe and target concentrations, solution chemistry, sequences of the probe and target, and temperature. For example, if the stem length is too large, it will be difficult for the stem-loop probe to open upon hybridization. On the other hand, if the stem length is too small, a large fraction of probes may open due to Brownian forces. Similarly, relative to the stem length, a longer probe may lead to a lower dissociation constant, however, it may also reduce the specificity, since the relative free energy change due to one-base mismatch would be smaller.

To further establish the structure-function relationships of probes, one can for example routinely design and synthesize a series of dual-FRET probes for targeting different K-ras codon 12 mutations, such as shown in Table 5. For each pair of donor and acceptor beacons, the donor beacon will contain one of the most common K-ras point mutations in pancreatic cancer such as GGT-GAT transitions (Gly to Asp) or GGT-GTT (Gly to Val), GGT-CGT (Gly to Arg), GGT-TGT (Gly to Cys) transversions. The same acceptor beacon can used with all donor beacons having different mutated sequences. As an example, a specific beacon design for nucleic acid probes of the present invention has a probe length of 21 nucleotides, a stem length of 4 nucleotides, and a gap size of 4 nucleotides between the donor and acceptor beacons bound on the same target. One can routinely examine the effect of beacon structure on hybridization rate and specificity by varying: 1) probe length of 17, 19 and 21 bases; 2) stem length of 4 and 5 bases; 3) gap sizes of 4 and 5 bases between donor and acceptor beacons along the target mRNA. For different parameter combinations, kinetic and thermodynamic modeling described above will be performed to build the analysis of the experimental data.

TABLE 5

Design of Molecular Beacons for K-ras Codon 12 Mutation

Wild-type K-ras (Bases 1–78)

```
 1 ATGACTGAAT ATAAACTTGT GGTAGTTGGA GCTGGTGGCG
41 TAGGcaagAG TGCCTTGACG ATACAGCTAA TTCAGAAT
   SEQ ID NO:27
```

Dual-FRET Molecular Beacons

Donor Beacon:    5'-Dabcyl-AGTGCGCTGTATCGTCAAGGCACT-6-Fam-3'
                 SEQ ID NO:28

Acceptor Beacon: 5'-Cy3-CCTACGCCATCAGCTCCGTAGG-Dabcyl-3'  Mut: GGT-GAT
                 SEQ ID NO:29

Acceptor Beacon: 5'-Cy3-CCTACGCCAACAGCTCCGTAGG-Dabcyl-3'  Mut: GGT-GTT
                 SEQ ID NO:30

TABLE 5-continued

Design of Molecular Beacons for K-ras Codon 12 Mutation

Acceptor Beacon: 5'-Cy3-CCTACGCCACGAGCTCC<u>GTAGG</u>-Dabcyl-3' Mut: GGT-CGT
SEQ ID NO:31

Acceptor Beacon: 5'-Cy3-CCTACGCCACAAGCTCC<u>GTAGG</u>-Dabcyl-3' Mut: GGT-TGT
SEQ ID NO:32

To further increase the detection sensitivity, for example, one can synthesize nucleic acid probes of the present invention to target a second cancer marker, such as survivin, which is expressed in pancreatic carcinomas but not in normal tissues.

To demonstrate the specificity of molecular beacons targeting K-ras point mutations, in-solution hybridization studies are carried out by mixing the donor nucleic acid probes of the present invention with respectively wild-type K-ras mRNA targets, the corresponding mutated K-ras mRNA targets and survivin targets at different probe/target concentrations. Thermal denaturation profiles are generated and the corresponding transition temperatures obtained. Since the detection specificity depends on the initial concentrations of probes and targets, the results of this study not only demonstrate the detection specificity but also provide guidelines for optimizing beacon delivery conditions. Furthermore, stopped-flow studies of the hybridization $k_1$netic rates are performed with each nucleic acid probe of the present invention design and each target type. This helps select the optimal structure of the nucleic acid probes of the present invention with the best possible combination of specificity and rate of hybridization.

To address potential issues with secondary structures of the mRNAs, synthetic targets with lengths three to four times the probe length are used in in-solution studies. To further utilize the nucleic acid probes of the present invention, total mRNAs of survivin and the mutant K-ras are isolated from pancreatic cancer cells known to carry them, amplified, and in-solution hybridization assays are performed to determine the extent of binding between the nucleic acid probes of the present invention and these mRNAs.

As mentioned earlier, in a cellular environment, nucleic acid probes can be degraded by cytoplasmic nucleases. To address this issue, the present invention provides probes synthesized with structural modifications such as 2'-O-methyl ODNs. Methylated-probe/target duplexes are more stable than DNA-probe/target duplexes, and methylated nucleic acid probes of the present invention hybridize to RNA targets faster than DNA probes. After delivery into primary human dermal fibroblast (HDF) cells, the fluorescence signal of unmodified molecular beacons with a random DNA sequence and methylated nucleic acid probes of the present invention with the same sequence are monitored over time to determine how long these probes can survive in a cellular environment.

To determine the specificity of the molecular beacons approach for detecting K-ras mutations in pancreatic cancer cells, nucleic acid probes of the present invention are synthesized to target four different K-ras codon 12 mutations (GGT-GAT, GGT-GTT, GGT-CGT and GGT-TGT). Delivery, hybridization and imaging assays are carried out using pancreatic cancer cell lines such as Panc-1 (GGT to GAT), Capan-1 (GGT to GTT), PSN-1 (GGT to CGT), and Miapaca-2 (GGT to TGT) with the corresponding mutant K-ras mRNAs. Also used is the pancreatic cell line BXPC-3 as a control which has the 'wild-type' K-ras mRNA.

Preliminary studies have shown that the K-ras codon 12 mutation GGT-GAT in Panc-1 cell lines has been confirmed. Further confirmation of the other three mutations (GGT-GTT, GGT-CGT and GGT-TGT) in the corresponding pancreatic cancer cell lines using PCR amplification of K-ras exon 1 sequence followed by DNA sequencing is routinely performed. The K-ras mRNA concentration in each cell line is also be quantified using real time RT-PCR. During a pilot study, the delivery, hybridization, and buffer conditions for the nucleic acid probes of the present invention have been optimized to target mutant K-ras mRNA in Panc-1 cells (with GGT to GAT mutation). As mentioned earlier, the invention provides a preferred condition for this type of probe of 150 µM of the probes in Opti-MEM 1 medium (GIBCO) and incubated at 37° C. for 30 to 60 minutes. It is anticipated that the optimal delivery and hybridization conditions for nucleic acid probes of the present invention targeting different mutant K-ras mRNAs may vary from those identified. Nucleic acid probes of the present invention designed for each specific K-ras mutation are incubated with at least four cell lines with the optimal delivery condition; these cell lines include the cell line containing the specific K-ras mutation, the 'wild-type' K-ras cell line BXPC-3, and two other cell lines with different K-ras mutations. The FRET-induced fluorescence signal in cells can be imaged using a confocal microscope. The specificity of the present probe detection methodology is confirmed when strong fluorescence signal are observed only in the cell line expressing the corresponding K-ras mutation but not in BXPC-3 nor other cell lines.

Similar assays are routinely performed to examine the specificity of survivin-targeting nucleic acid probes of the present invention using pancreatic cancer cell lines expressing different levels of survivin gene as well as the normal human fibroblast cells as a control. For example, using RT-PCR and Northern blotting, the level of survivin expression in pancreatic cell line Miapaca-2 ihas been found to be high, in BXPC-3 it is much lower, while in HDF the expression level is almost zero. The probe sequence of the survivin probes is shown in Table 6 and the steps of the assay are similar to that described above. The tumor cell lines expressing different levels of survivin mlNA and the normal cell line HDF are incubated with the survivin nucleic acid probes of the present invention, and the resulting fluorescence are imaged using a confocal microscope.

TABLE 6

Design of Molecular Beacons for Survivin mRNA

Survivin (bases 1-121)

```
 1 A TGGGTGCCCC GACGTTGCCC CCTGCCTGGC AGCCCTTTCT
42 CAAGGaccaC CGCATCTCTA CATTCAAGAA CTGGCCCTTC
82 TTGGAGGGCT GCGCCTGCAC CCCGGAGCGG ATGGCCGAGG
   SEQ ID NO:33
```

Dual-FRET Molecular Beacons

Donor Beacon:   5'-Alexa546-CCTTGAGAAAGGGCTGCCCAAGG-Dabcyl-3'
                SEQ ID NO:34

Acceptor Beacon: 5'-Dabcyl-CCGCATTGAATGTAGAGATGCGG-Texas Red-3'
                 SEQ ID NO:35

A critical issue concerning the specificity of detecting pancreatic cancer cells is that both K-ras codon 12 mutations and survivin are being expressed in colorectal and lung cancers as well. To assure high specificity for detecting cancer cells originated from the pancreatic ducts, in addition to using nucleic acid probes of the present invention targeting survivin and K-ras mutations, a third probe pair for the chymotrypsinogen gene can be synthesized, which is pancreas-specific. An example of the design of donor and acceptor probes are respectively: donor probe: 5'- AMCA-ACCTGGATGTTGTCCTCGTCAGGT-dabcyl-3' SEQ ID NO:36 and acceptor probe: 5'-dabcyl-AAGATTGAAGA-CCTTGGCGATCTT-Diakylaminocoumarin-3' (underlined bases are complementary bases to form a stem) SEQ ID NO:37. This nucleic acid probe pair of the present invention will be delivered into pancreatic, lung and colon cancer cell lines as well as the normal human fibroblast cell line HDF and the resulting fluorescence images recorded. This will assure that only cells originated from pancreatic duct are detected. All the detection assays with cells are performed at 37° C. The assays determining detection specificity with lanthanide-dye based nucleic acid probes of the present invention are carried out using a Safire monochromator reader (Tecan).

To determine the sensitivity of the probe-based methodology in detecting pancreatic cancer cells, pancreatic cancer and normal cells are mixed with 1:1,000 (i.e., one cancer cell in 1,000 normal cells), 1:10,000, 1:100,000 and 1:1,000,000 ratios and incubate the mixture with the dual-FRET molecular beacons designed for the specific cancer cell line under optimized conditions (probe concentration and duration). After placing cells on glass coverslips, FRET-induced fluorescence images of the hybridized nucleic acid probes of the present invention in cancer cells are obtained using a confocal microscope. Further, a FACS Vantage SE cell sorter (Becton-Dickinson) is used to sort out the cancer cells in the mixture in suspension. The cell sorter, which has a sorting sensitivity of 1:100,000, has three excitation wavelengths: 488 nm, 547 nm, and UV. The fluorescence emission due to dual-FRET probes in cells can be detected by using the proper filter. The dual-FRET probe pairs for detecting survivin, K-ras mutations and chymotrypsinogen are so designed such that the donor dye molecules are respectively excited with laser at 353 nm, 488 nm and 547 nm. A fluorescence intensity threshold in the detection is chosen such that the effect of background due to auto-fluorescence of cells and digested nucleic acid probes of the present invention is minimized. In this study, the pancreatic cell lines Panc-1, Capan-1, PSN-1 and Miapaca-2 are used as cancer cells, and a human dermal fibroblast cell line (HDF) serves as normal cells.

In obtaining images of hybridized molecular beacons in cancer cells, having ultra-sensitive fluorescence measurements is important, since typically only a very small number of cancer cells are present in a sample. The FACS Vantage Flow Cytometer (cell sorter) will be used due to its very high detection sensitivity, capability of 5 color analysis and sorting, wide flexibility of excitation wavelengths, and cross beam laser compensation for separation of overlapping excitation. An imaging analysis will also be carried out to enhance the results of FRET fluorescence measurements. In this example, in carrying out imaging assays of detection sensitivity, only nucleic acid probes of the present invention with organic dye pairs for FRET will be used, since currently the Zeiss confocal microscope and the FACS cell sorter do not have an imaging capability with time resolved FRET.

This example is based on the rational that detection of tumor markers including survivin and mutant K-ras mRNAs in pancreatic duct cells using dual-FRET nucleic acid probes of the present invention can lead to early diagnosis of pancreatic cancer especially in high-risk patients. It demonstrates that the novel dual-FRET molecular beacons methodology of the present invention has the potential to become a simple clinical procedure for early detection of pancreatic cancer with high sensitivity, specificity, signal-to-noise ratio, and efficiency. This is further demonstrated with subsequent translational research using clinical samples. The same methodology can be rountinely extended to the early detection and diagnosis of other cancers, and the study of gene expression in live cells relevant to solving other biomedical problems.

REFERENCES

Bemacchi, S., and Y. Mely. 2001. Exciton interaction in molecular beacons: a sensitive sensor for short range modifications of the nucleic acid structure. *Nucleic Acids Res.* 29:E62-2.

Bonnet, G., S. Tyagi, A. Libchaber, and F. R. Kramer. 1999. Thermodynamic basis of the enhanced specificity of structured DNA probes. *Proc. Natl. Acad. Sci. USA* 96: 6171–6176.

Bonnet, G., Krichevsky, O. and Libchaber, A. 1998. Kinetics of conformational fluctuations in DNA hairpin-loops. *Proc. Natl. Acad. Sci. USA,* 95, 8602–8606.

Cardullo, R. A., Agrawal, S., Flores, C., Zamecnik, P. C., Wolf, D. E. 1998. Detection of nucleic acid hybridization by nonradiative fluorescence resonance energy transfer. *Proc. Natl. Acad. Sci. USA.* 85, 8790–8794.

Chen, W., Martinez, G. and Mulchandani, A. 2000 Molecular beacons: a real-time polymerase chain reaction assay for detecting Salmonella. *Anal. Biochem.,* 280, 166–172.

Cooper, M., and P. Sammes. 2000. Synthesis and spectral properties of a new luminescent europium(III) terpyridyl chelate. *J Chem. Soc. Perkin. Trans.* 2:1695–1700.

de Baar, M. P., Timmermans, E. C., Bakker, M., de Rooij, E., van Gemen, B. and Goudsmit, J. 2001 One-tube real-time isothermal amplification assay to identify and distinguish human immunodeficiency virus type 1 subtypes A, B, and C and circulating recombinant forms AE and AG. *J. Clin. Microbiol.,* 39, 1895–1902.

Dirks, R. W., C. Molenaar and H. J. Tanke. 2001. Methods for visualizing RNA processing and transport pathways in living cells. *Histochem. Cell Biol.* 115:3–11.

Elangovan M, R. N. Day, and A. Periasamy. 2002. Nanosecond fluorescence resonance energy transfer-fluorescence lifetime imaging microscopy to localize the protein interactions in a single living cell. *J. Microsc.* 205:3–14.

Evangelista, R. A., A. Pollak, B. Allore, E. F. Templeton, R. C. Morton, and E. P. Diamandis. 1988. A new europium chelate for protein labelling and time-resolved fluorometric applications. *Clin. Biochem.* 21:173–178.

Fang, X., J. J. Li, and W. Tan. 2000. Using molecular beacons to probe molecular interactions between lactate dehydrogenase and single-stranded DNA. *Anal. Chem:* 72:3280–3285.

Femino, A. M, F. S., Fay, K. Fogarty, and R. H. Singer. 1998. Visualization of single RNA transcripts in situ. *Science* 280:585–90.

Goddard, N. L., Bonnet, G., Krichevsky, O., Libchaber, A. 2000. Sequence dependent rigidity of single stranded DNA. *Phys. Rev. Lett.,* 85, 2400–2403.

Hung, S. C., R. A. Mathies, and A. N. Glazer. 1997. Optimization of spectroscopic and electrophoretic properties of energy transfer primers. *Analytical Biochemistry* 252:78–88.

Ju, J., I. Kheterpal, J. R. Scherer, C. Ruan, C. W. Fuller, A. N. Glazer, and R. A. Mathies. 1995. Design and synthesis of fluorescent energy transfer dye-labeled primers and their application for DNA sequencing and analysis. *Analytical Biochemistry* 231:131–40.

Kang J. S., J. R. Lakowicz, and G. Piszczek. 2002. DNA dynamics: a fluorescence resonance energy transfer study using a long-lifetime metal-ligand complex. *Arch. Pharm. Res.* 25:143–150.

Klostermeier D, and D. P. Millar. 2002. Time-resolved fluorescence resonance energy transfer: A versatile tool for the analysis of nucleic acids. *Biopolymers* 61:159–179.

Kuhn, H., Demidov, V. V., Coull, J. M., Fiandaca, M. J., Gildea, B. D. and Frank-Kamenetski, M. D. 2002. Hybridization of DNA and PNA molecular beacons to single-stranded and double-stranded DNA targets. *J. Am Chem Soc.,* 124, 1097–1103.

Li, J. J., R. Geyer, and W. Tan. 2000. Using molecular beacons as a sensitive fluorescence assay for enzymatic cleavage of single-stranded DNA. *Nucleic Acids Res.* 28:E52.

Li, M. and P. R. Selvin. 1997. Amine-reactive forms of a luminescent diethylenetriaminepentaacetic acid chelate of terbium and europium: attachment to DNA and energy transfer measurements. *Bioconjug. Chem.* 8:127–132.

Liu, J., P. Feldman, and T. D. Chung. 2002. Real-time monitoring in vitro transcription using molecular beacons. *Anal. Biochem.* 300:40–45.

Lemmetyinen, H., E. Vuorimaa, A. Jutila, V. M. Mukkala, H. Takalo, and J. Kankare. 2000. A time-resolved study of the mechanism of the energy transfer from a ligand to the lanthanide(III) ion in solutions and solid films. *Luminescence* 15:341–350.

Lopez, E., C. Chypre, B. Alpha, and G. Mathis. 1993. Europium(III) trisbipyridine cryptate label for time-resolved fluorescence detection of polymerase chain reaction products fixed on a solid support. *Clin. Chem.* 39:196–201.

Marras, S. A., Kramer, F. R. and Tyagi, S. (1999) Multiplex detection of single-nucleotide variations using molecular beacons. *Genet. Anal,* 14, 151–156.8.

Matsuo, T. 1998. In situ visualization of messenger RNA for basic fibroblast growth factor in living cells. *Biochim. Biophys. Acta* 1379:178–184.

Mergny, J. L., A. S. Boutorine, T. Garestier, F. Belloc, M. Rougee, N. V. Bulychev, A. A. Koshkin, J. Bourson, A. V. Lebedev, and B. Valeur. 1994. Fluorescence energy transfer as a probe for nucleic acid structures and sequences. *Nucleic Acids Res.* 22: 920–928.

Mitchell, P. 2001. Turning the spotlight on cellular imaging. *Nat. Biotechnol.* 19:1013–1017.

Molenaar, C., S. A. Marras, J. C. Slats, J. C. Truffert, M. Lemaitre, A. K. Raap, R. W. Dirks, and H. J. Tanke. 2001. Linear 2'O-Methyl RNA probes for the visualization of RNA in living cells. *Nucleic Acids Res.* 29:E89-9.

Morrison, L. E., and L. M. Stols. 1993. Sensitive fluorescence-based thermodynamic and kinetic measurements of DNA hybridization in solution. *Biochemistry.* 32:3095–3104.

Ratilainen, T., Holmen, A., Tuite, E., Haaima, G., Christensen, L., Nielsen, P. E. and Norden, B. 1998. Hybridization of peptide nucleic acid. *Biochemistry,* 37, 12331–12342.

Sei-Iida, Y., H. Koshimoto, S. Kondo, and A. Tsuji. 2000. Real-time monitoring of in vitro transcriptional RNA synthesis using fluorescence resonance energy transfer. *Nucleic Acids Res.* 28:E59.

Sixou, S., F. C. Szoka, Jr., G. A. Green, B. Giusti, G. Zon, and D. J. Chin. 1994. Intracellular oligonucleotide hybridization detected by fluorescence resonance energy transfer (FRET). *Nucleic Acids Res.* 22:662–668.

Sokol, D. L., X. Zhang, P. Lu, and A. M. Gewirtz. 1998. Real time detection of DNA.RNA hybridization in living cells. *Proc. Natl. Acad. Sci. USA* 95:11538–11543.

Sueda, S., J. Yuan, and K. Matsumoto. 2000. Homogeneous DNA hybridization assay by using europium luminescence energy transfer. *Bioconjug. Chem.* 11:827–831.

Tsourkas, A., M. Behlke, S. Rose, and G. Bao. 2002a. Hybridization kinetics and thermodynamics of molecular beacons, submitted to *Biophysical J.*

Tsourkas, A., M. Behlke, and G. Bao. 2002b. Structure-function relationships of shared-stem and conventional molecular beacons, submitted to *Nucleic Acids Res.*

Tsourkas, A. and Bao, G. 2001. Detecting mRNA transcripts using FRET-enhanced molecular beacons. In Proceedings of the 2001 *Bioengineering Conference,* ASME BED-Vol. 50, pp. 169–170.

Tsuji, A., Y. Sato, M. Hirano, T. Suga, H. Koshimoto, T. Taguchi, and S. Ohsuka 2001. Development of a time-resolved fluorometric method for observing hybridization in living cells using fluorescence resonance energy transfer. *Biophys J.* 81:501–515.

Tsuji, A., H. Koshimoto, Y. Sato, M. Hirano, Y. Sei-Iida, S. Kondo, and K. Ishibashi. 2000. Direct observation of specific messenger RNA in a single living cell under a fluorescence microscope. *Biophys J.* 78:3260–3274.

Tyagi, S. and F. R. Kramer. 1996. Molecular beacons: probes that fluoresce upon hybridization. *Nat. Biotechnol.* 14:303–308.

Vogelstein, B. and Kinzler, K. W. 1999. Digital PCR. *Proc. Natl. Acad. Sci. USA,* 96, 9236–9241.

Yuan, J., K. Matsumoto, and H. Kimura. 1998. A new tetradentate beta-diketonate-europium chelate that can be covalently bound to proteins for time-resolved fluoroimmunoassay. *Anal. Chem.* 70:596–601.

Zuker, M. 2000. Calculating nucleic acid secondary structure. *Curr. Opin. Struct. Biol.* 10, 303–310.

Throughout this application, various publications are referenced. The disclosures of all of these publications and those references cited within those publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and Examples be considered as exemplary only. Those skilled in the art will recognize, or will be able to ascertain using no more than routine experimentation, many equivalents to the specific embodiments of the invention described herein. Such equivalents are intended to be encompassed by the following claims.

We claim:

1. A composition for detection of a subject nucleic acid comprising,
    a. a first nucleic acid probe that hybridizes to a first nucleic acid target sequence on the subject nucleic acid, forms a stem-loop structure when not bound to the first nucleic acid target sequence, and incorporates a resonance energy transfer donor moiety; and
    b. a second nucleic acid probe that hybridizes to a second nucleic acid target sequence on the subject nucleic acid, forms a stem-loop structure when not bound to the second nucleic acid target sequence, and incorporates a resonance energy transfer acceptor moiety, wherein the first nucleic acid target sequence and the second nucleic acid target sequence are separated by a number of nucleotides on the subject nucleic acid such that a resonance energy transfer signal from interaction between the donor moiety of the first nucleic acid probe and the acceptor moiety of the second nucleic acid probe can be detected to determine hybridization of both the first nucleic acid probe and the second nucleic acid probe to the subject nucleic acid.

2. The composition of claim 1, wherein the first nucleic acid probe further incorporates a quencher moiety, such that an interaction between the donor moiety of the first nucleic acid probe and the quencher moiety can be detected to differentiate between the first nucleic acid probe in the stem-loop structure and non-stem-loop structure.

3. The composition of claim 1, wherein the second nucleic acid probe further incorporates a quencher moiety, such that an interaction between the acceptor moiety of the second nucleic acid probe and the quencher moiety can be detected to differentiate between the second nucleic acid probe in the stem-loop structure and non-stem-loop structure.

4. The composition of claim 1, wherein the first nucleic acid probe further incorporates a resonance energy transfer acceptor moiety, such that a resonance energy transfer signal from interaction between the donor moiety and the acceptor moiety on the first nucleic acid probe can be detected to differentiate between the first nucleic acid probe in the stem-loop structure and non-stem-loop structure.

5. The composition of claim 1, wherein the second nucleic acid probe further incorporates a resonance energy transfer donor moiety, such that a resonance energy transfer signal from interaction between the donor moiety and the acceptor moiety on the second nucleic acid probe can be detected to differentiate between the second nucleic acid probe in the stem-loop structure and non-stem-loop structure.

6. The composition of claim 1, wherein the resonance energy transfer signal is due to fluorescence resonance energy transfer.

7. The composition of claim 1, wherein the resonance energy transfer signal is due to fluorescence resonance energy transfer and the donor moiety is 6-Fam fluorophore.

8. The composition of claim 1, wherein the resonance energy transfer signal is due to fluorescence resonance energy transfer and the acceptor moiety is Cy-3, ROX or Texas Red.

9. The composition of claim 1, wherein the resonance energy transfer signal is due to luminescence resonance energy transfer.

10. The composition of claim 1, wherein the resonance energy transfer signal is due to luminescence resonance energy transfer and the donor moiety is a lanthanide chelator molecule.

11. The composition of claim 1, wherein the resonance energy transfer signal is due to luminescence resonance energy transfer and the donor moiety is Europium or Terbium.

12. The composition of claim 1, wherein the resonance energy transfer signal is due to luminescence resonance energy transfer and the donor moiety is a lanthanide chelator molecule selected from DTPA-cytosine, DTPA-cs124, BCPDA, BHHCT, Isocyanato-EDTA, Quantum Dye, or W1024.

13. The composition of claim 1, wherein the donor moiety is a lanthanide chelate and the acceptor moiety is an organic dye, Cy3, Cy5, ROX or Texas Red, or a phycobiliprotein.

14. The composition of claim 1, wherein the acceptor moiety is a phycobiliprotein selected from Red Phycoerythrin (RPE), Blue Phycoerythrin (BPE), or Allophycocyanin (APC).

15. The composition of claim 1, wherein the first or second nucleic acid probes comprises 5 to 50 nucleotides.

16. The composition of claim 1, wherein the first or second nucleic acid probes comprises 10 to 40 nucleotides.

17. The composition of claim 1, wherein the first or second nucleic acid probes comprises 15 to 30 nucleotides.

18. The composition of claim 1, wherein the first or second nucleic acid probes comprises 20 to 25 nucleotides.

19. The composition of claim 1, wherein the first or second nucleic acid probes comprises a 2'-O-methyl nucleotide backbone.

20. The composition of claim 1, wherein one end of the first or second nucleic acid probes participates in both stem-loop formation and hybridization to the nucleic acid target sequence.

21. The composition of claim 1, wherein the first nucleic acid target sequence and the second nucleic acid target sequence are separated by 1 to 20 nucleotides.

22. The composition of claim 1, wherein the first nucleic acid target sequence and the second nucleic acid target sequence are separated by 2 to 10 nucleotides.

23. The composition of claim 1, wherein the first nucleic acid target sequence and the second nucleic acid target sequence are separated by 3 to 7 nucleotides.

24. A composition for detection of a subject nucleic acid comprising,
   a. a first nucleic acid probe that hybridizes to a first nucleic acid target sequence on the subject nucleic acid, and incorporates a luminescence resonance energy transfer lanthanide chelate donor moiety; and
   b. a second nucleic acid probe that hybridizes to a second nucleic acid target sequence on the subject nucleic acid, and incorporates an organic resonance energy transfer acceptor moiety, wherein the first nucleic acid target sequence and the second nucleic acid target sequence are separated by a number of nucleotides on the subject nucleic acid such that a luminescence resonance energy transfer signal from interaction between the lanthanide chelate donor moiety of the first nucleic acid probe and the acceptor moiety of the second nucleic acid probe can be detected to determine hybridization of both the first nucleic acid probe and the second nucleic acid probe to the subject nucleic acid.

25. The composition of claim 24, wherein the first nucleic acid probe or second nucleic acid probe is linear or randomly coiled when not hybridized to the first or second nucleic acid target sequences, respectively.

26. The composition of claim 24, wherein the first nucleic acid probe or second nucleic acid probe forms a stem-loop structure when not hybridized to the first or second nucleic acid target sequences, respectively.

27. The composition of claim 26, wherein the first nucleic acid probe further incorporates a quencher moiety, such that an interaction between the donor moiety of the first nucleic acid probe and the quencher moiety can be detected to differentiate between the first nucleic acid probe in the stem-loop structure and non-stem-loop structure.

28. The composition of claim 26, wherein the second nucleic acid probe further incorporates a quencher moiety, such that an interaction between the acceptor moiety of the second nucleic acid probe and the quencher moiety can be detected to differentiate between the second nucleic acid probe in the stem-loop structure and non-stem-loop structure.

29. The composition of claim 24, wherein the lanthanide donor moiety is Europium or Terbium.

30. The composition of claim 24, wherein the donor moiety is selected from a lanthanide chelate DTPA-cytosine, DTPA-cs124, BCPDA, BHHCT, Isocyanato-EDTA, Quantum Dye, or W1024.

31. The composition of claim 24, wherein the donor moiety is a lanthanide chelate and the acceptor moiety is an organic dye or a phycobiliprotein.

32. The composition of claim 24, wherein the acceptor moiety is a phycobiliprotein selected from Red Phycoerythrin (RPE), Blue Phycoerythrin (BPE), or Allophycocyanin (APC).

33. The composition of claim 24, wherein the second nucleic acid probe comprises a plurality of acceptor moieties.

34. The composition of claim 24, wherein the first or second nucleic acid probes comprises 5 to 50 nucleotides.

35. The composition of claim 24, wherein the first or second nucleic acid probes comprises 10 to 40 nucleotides.

36. The composition of claim 24, wherein the first or second nucleic acid probes comprises 15 to 30 nucleotides.

37. The composition of claim 24, wherein the first or second nucleic acid probes comprises 20 to 25 nucleotides.

38. The composition of claim 24, wherein the nucleic acid probes comprises a 2'-O-methyl nucleotide backbone.

39. The composition of claim 24, wherein one end of either the first or the second nucleic acid probes participates in both stem-loop formation and hybridization to the target sequence nucleic acid.

40. The composition of claim 24, wherein the first nucleic acid target sequence and the second nucleic acid target sequence are separated by 1 to 20 nucleotides.

41. The composition of claim 24, wherein the first nucleic acid target sequence and the second nucleic acid target sequence are separated by 2 to 10 nucleotides.

42. The composition of claim 24, wherein the first nucleic acid target sequence and the second nucleic acid target sequence are separated by 3 to 7 nucleotides.

43. A method of detecting a subject nucleic acid, comprising combining the composition of claim 1 or claim 24 with a sample suspected of containing the subject nucleic acid, and detecting hybridization by resonance energy transfer signals to determine the presence or absence of the subject nucleic acid in the sample.

44. The method of claim 43, wherein the method is performed in vivo.

45. The method of claim 44, wherein the sample contains a living cell.

46. The method of claim 43, wherein the subject nucleic acid comprises a genetic point mutation, deletion or insertion relative to a control nucleic acid.

47. The method of claim 43, wherein the detection of the subject nucleic acid indicates the presence of a cancer in the sample.

48. The method of claim 43, wherein the subject nucleic acid comprises K-ras, survivin, p53, p16, DPC4, or BRCA2.

49. The method of claim 43, wherein the detection of the subject nucleic acid indicates an alteration of the expression pattern of the subject nucleic acid in response to an external stimulus.

50. The method of claim 43, wherein the detection is performed with single- or multiple-photon microscopy, time-resolved fluorescence microscopy or fluorescence endoscopy.

* * * * *

UNITED STATES PATENT AND TRADEMARK OFFICE
CERTIFICATE OF CORRECTION

| | |
|---|---|
| PATENT NO. | : 7,081,336 B2 |
| APPLICATION NO. | : 10/179730 |
| DATED | : July 25, 2006 |
| INVENTOR(S) | : Gang Bao, Andrew Tsourkas and Yangqing Xu |

It is certified that error appears in the above-identified patent and that said Letters Patent is hereby corrected as shown below:

Claim 15, line 6, replace "comprises" with --comprise--.
Claim 16, line 8, replace "comprises" with --comprise--.
Claim 17, line 10, replace "comprises" with --comprise--.
Claim 18, line 12, replace "comprises" with --comprise--.
Claim 19, line 14, replace "comprises" with --comprise--.
Claim 19, line 14, replace "2'-O-methyl" with --2'-*O*-methyl--.
Claim 20, line 18, replace "first or second" with --nucleic--.
Claim 24, line 40, replace "on" with --in--.
Claim 34, line 18, replace "comprises" with --comprise--.
Claim 35, line 20, replace "comprises" with --comprise--.
Claim 36, line 22, replace "comprises" with --comprise--.
Claim 37, line 24, replace "comprises" with --comprise--.
Claim 38, line 26, replace "comprises" with --comprise--.
Claim 38, line 26, replace "2'-O-methyl" with --2'-*O*-methyl--.
Claim 39, line 28, replace "the first or the second" with --first or second--.
Claim 39, lines 29 and 30, replace "target sequence nucleic acid" with --nucleic acid target sequence--.
Claim 44, line 47, replace "in vivo" with --*in vivo*--.
Claim 48, line 47, replace "K-ras" with --K-*ras*--, replace "p53" with --*p53*--, and replace "p16" with --*p16*--.

Signed and Sealed this

Thirty-first Day of July, 2007

JON W. DUDAS
*Director of the United States Patent and Trademark Office*